(12) United States Patent
Sidebotham et al.

(10) Patent No.: US 11,559,313 B2
(45) Date of Patent: *Jan. 24, 2023

(54) RADIAL SAW BLADE AND HUB FOR OSTEOTOMY

(71) Applicant: BioMedtrix, LLC, Whippany, NJ (US)

(72) Inventors: Christopher G. Sidebotham, Mendham, NJ (US); Gregory Thomas Van Der Meulen, Ketchum, ID (US); Joshua French, Budd Lake, NJ (US)

(73) Assignee: BioMedtrix, LLC, Whippany, NJ (US)

( * ) Notice: Subject to any disclaimer, the term of this patent is extended or adjusted under 35 U.S.C. 154(b) by 41 days.

This patent is subject to a terminal disclaimer.

(21) Appl. No.: 16/919,914

(22) Filed: Jul. 2, 2020

(65) Prior Publication Data

US 2020/0330104 A1    Oct. 22, 2020

Related U.S. Application Data

(63) Continuation of application No. 15/807,333, filed on Nov. 8, 2017, now Pat. No. 10,702,283.

(Continued)

(51) Int. Cl.
*A61B 17/14* (2006.01)
*A61B 17/15* (2006.01)
(Continued)

(52) U.S. Cl.
CPC .......... *A61B 17/147* (2016.11); *A61B 17/154* (2013.01); *A61B 17/1637* (2013.01);
(Continued)

(58) Field of Classification Search
CPC ...... B23D 51/10; B23D 51/01; B23D 61/123; B23D 61/006; B23D 61/025; B23D 49/10;
(Continued)

(56) References Cited

U.S. PATENT DOCUMENTS

| 4,409,973 A | 10/1983 | Neufeld |
| 4,736,928 A | 4/1988 | Smilkstein |

(Continued)

OTHER PUBLICATIONS

SECUROS Catalog pp. 114 and 115, Secures Surgical, Jul. 17, 2014, 3pps.

(Continued)

*Primary Examiner* — Marcela I. Shirsat
(74) *Attorney, Agent, or Firm* — Klarquist Sparkman, LLP

(57) ABSTRACT

A saw blade includes a main body having a first surface, a second surface on an opposite side of the main body from the first surface, a proximal edge portion, a distal edge portion, and first and second side portions extending between the proximal and distal edge portions. The proximal edge portion is configured to be coupled to a rotatable hub such that the saw blade is held in a curved shape with the first surface defining an outer radius when the saw blade is coupled to the rotatable hub. The distal edge portion includes a plurality of cutting teeth, and the second surface includes a cutting structure configured such that a radius of an arc swept by the cutting structure when the saw blade is rotated is substantially equal to the outer radius of the first surface.

21 Claims, 19 Drawing Sheets

Related U.S. Application Data

(60) Provisional application No. 62/420,437, filed on Nov. 10, 2016.

(51) Int. Cl.
| | | |
|---|---|---|
| *A61B 17/16* | (2006.01) | |
| *B23D 61/02* | (2006.01) | |
| *B23D 61/12* | (2006.01) | |
| *A61B 17/00* | (2006.01) | |
| *A61B 17/3213* | (2006.01) | |
| *B23D 67/04* | (2006.01) | |
| *B26B 21/52* | (2006.01) | |
| *B26D 1/00* | (2006.01) | |

(52) U.S. Cl.
CPC ........... *A61B 17/142* (2016.11); *A61B 17/157* (2013.01); *A61B 17/3213* (2013.01); *A61B 2017/00477* (2013.01); *B23D 61/025* (2013.01); *B23D 61/123* (2013.01); *B23D 61/125* (2013.01); *B23D 67/04* (2013.01); *B26B 21/521* (2013.01); *B26D 2001/006* (2013.01); *Y10T 83/4749* (2015.04); *Y10T 83/7045* (2015.04)

(58) Field of Classification Search
CPC ...... B23D 49/11; B23D 49/156; B23D 57/00; B23D 67/04; B23D 45/044; B23D 45/048; B26D 7/086; B26D 2001/006; B26B 9/00; B26B 9/02; B26B 25/002; B26B 5/00; B26B 21/56; B26B 21/225; B26B 21/521; B25G 3/00; A61B 17/3213; A61B 17/14; A61B 17/142; A61B 17/147; A61B 17/157; A61B 17/154; A61B 17/1637; A61B 17/1659; A61B 2017/320028; A61B 2017/00477; Y10T 83/4749; Y10T 83/6985; Y10T 83/7045; Y10T 83/7788; Y10T 83/7793; Y10T 83/8798; Y10T 83/9481
USPC .................. 30/339–340, 342–343, 355, 357, 30/392–394, 301; 83/315, 769, 782, 490, 83/491, 597, 839, 699.21; 606/82, 171, 606/176, 167, 178, 177, 79–85

See application file for complete search history.

(56) References Cited

U.S. PATENT DOCUMENTS

| | | | | |
|---|---|---|---|---|
| 4,768,504 | A | * | 9/1988 | Ender .................. A61B 17/142 606/177 |
| 4,955,888 | A | | 9/1990 | Slocum |
| 5,263,972 | A | * | 11/1993 | Evans .................... B23D 51/10 606/176 |
| 7,727,234 | B2 | * | 6/2010 | Thorsgard .............. A61B 17/15 606/82 |
| 8,523,868 | B2 | * | 9/2013 | Boykin ................ A61B 17/142 606/82 |

OTHER PUBLICATIONS

Carpenter, "BioDur 316LS Stainless," Secle Division Medica, Carpenter, Nov. 22, 2005, https://www.scecle.com/fichatec.pdf.

Carpenter BioDur™ 316LS Stainless Medical Implant Alloy, 70% Cold Worked, http://www.matweb.com/search/DataSheet.aspx7MatGUID=b666b6b611eb4848953dbfel67236762, (Year: Copyright 1996-2019).

Farrell et al., "In Vitro Performance Testing of Two Arcuate Oscillating Saw Blades Designed for Use During Tibial Plateau Leveling Osteotomy," Veterinary Surgery 40: 694-707, 2011.

Moutrey, "Chapter 1: Basic Surgical Techniques and Instrument Classification," The Fundamentals of Surgical Instruments: A practical guide to their recognition, use and care, TFM Publishing Ltd., 2017 (21 pages).

\* cited by examiner

Cranial Cruciate Ligament (CCL)
Thrust resisted by CCL

FIG. 6A
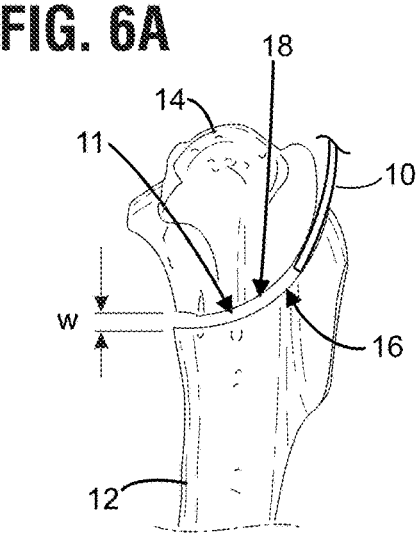
FIG. 6B
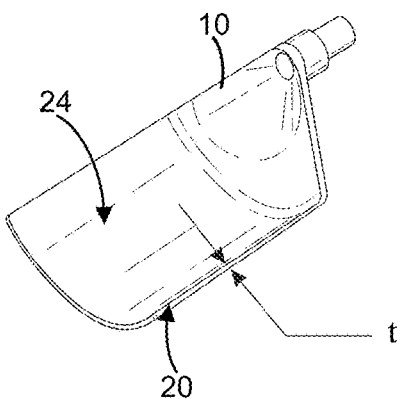
FIG. 7A
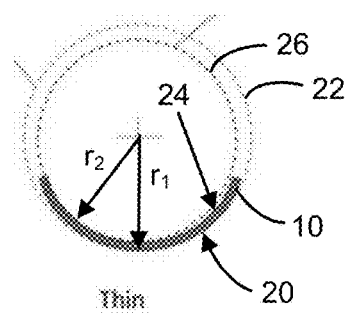
Thin
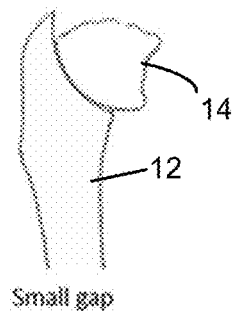
Small gap
FIG. 7B
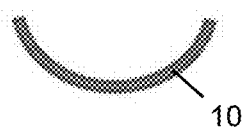
Medium
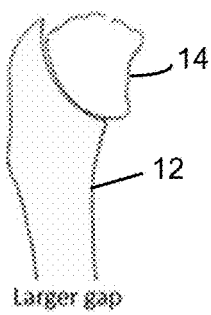
Larger gap
FIG. 7C
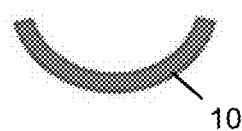
Thick
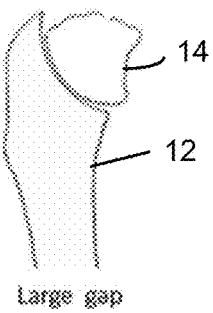
Large gap

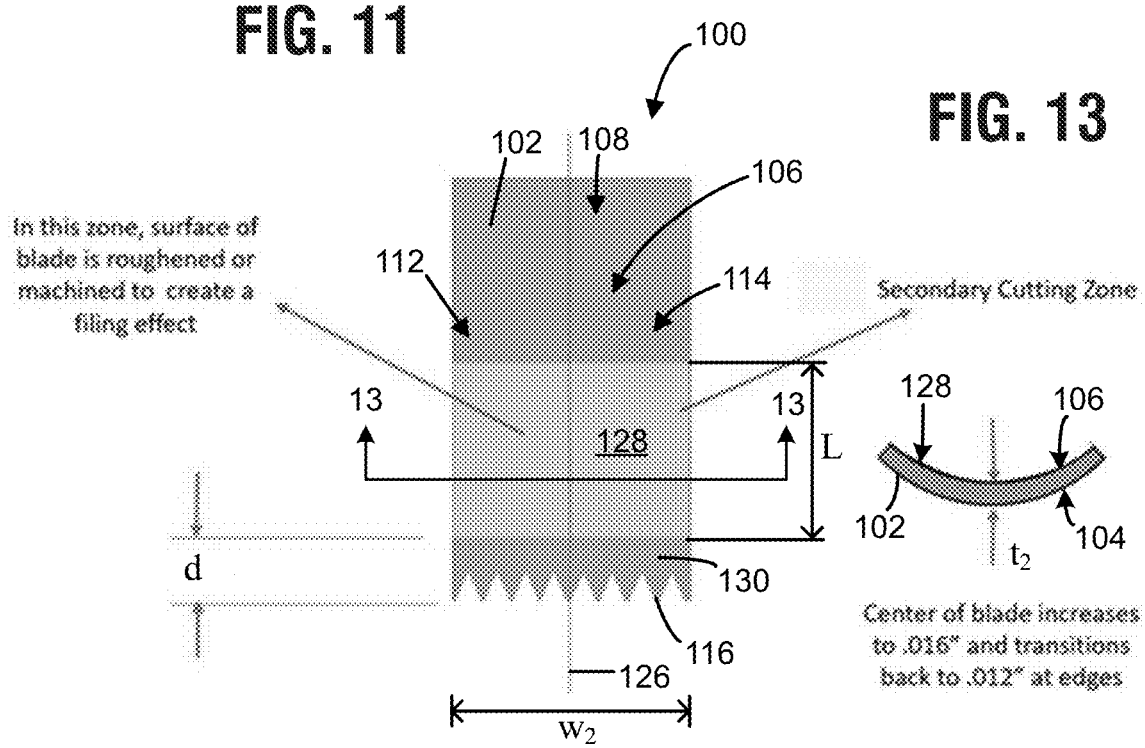
FIG. 11
FIG. 13
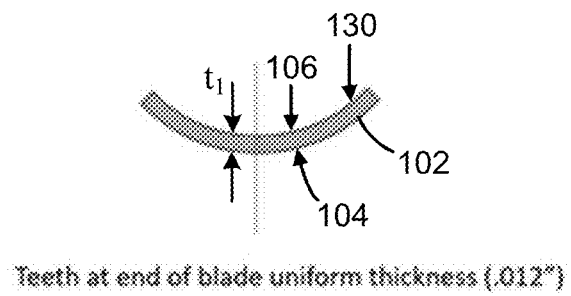
FIG. 12

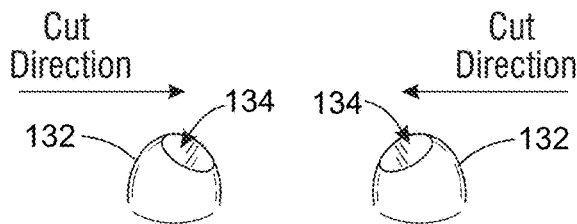
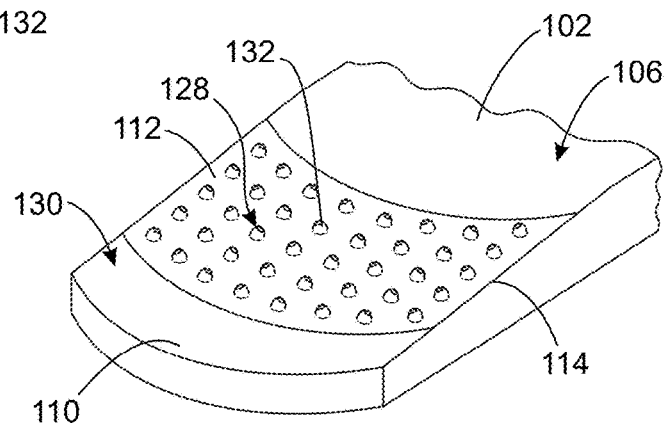
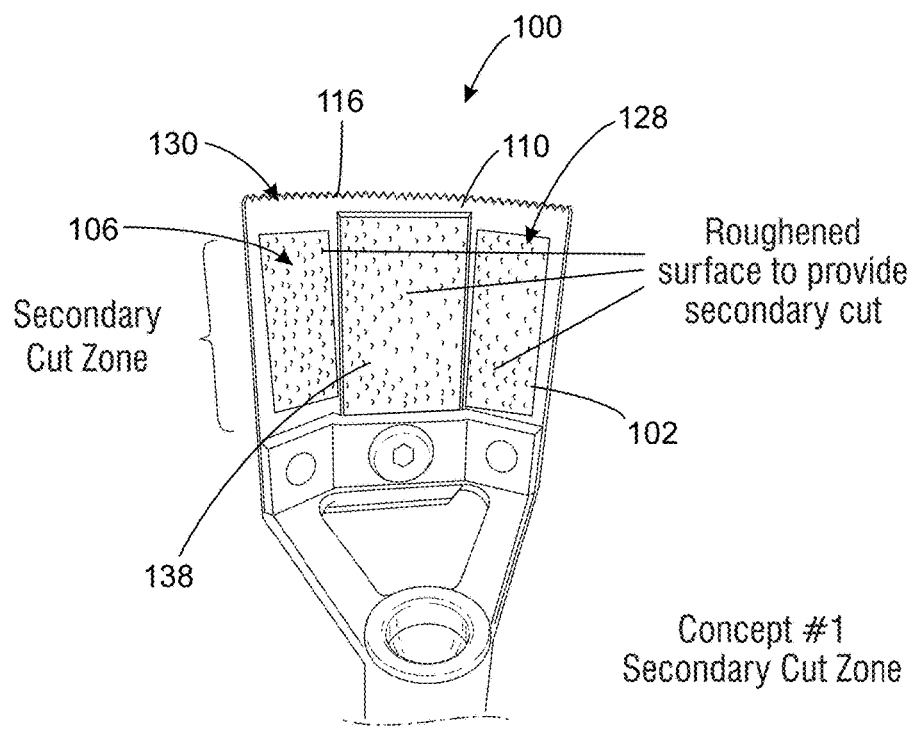

At the crest of each wave, the tooth runs from the crest to the base (outside radius side) creating different tooth heights along the cutting edge of the blade Conventional Sawblade Conventional sawblade with inner and outer radii which are different.

Resultant Fit from New Sawblade

New sawblade has ability to generate the same radius on the inside and outside for an improved fit.

RADIAL SAW BLADE AND HUB FOR OSTEOTOMY

CROSS REFERENCE TO RELATED APPLICATION

This application is a continuation of U.S. application Ser. No. 15/807,333 filed Nov. 8, 2017, which claims the benefit of U.S. Provisional Application No. 62/420,437, filed Nov. 10, 2016. Each of U.S. application Ser. No. 15/807,333 and U.S. Provisional Application No. 62/420,437 are incorporated herein by reference herein in their entirety.

FIELD

This application pertains to saw blades and hub assemblies for osteotomy procedures.

BACKGROUND

Radial saw blades used to create osteotomies during orthopedic procedures remove bone material as the cut is made. Depending upon the procedure, the resultant cut surfaces may be repositioned against each other and stabilized with bone plates, screws, or other devices. Large gaps between the two osteotomy surfaces created by the geometry of the saw blade can result in instability when the surfaces are mated. This can lengthen recovery time, and increase the potential for post-operative complications. Additionally, many existing blade and hub designs are complex and costly to manufacture, making frequent replacement cost-prohibitive. Accordingly, a need exists for improved saw blades for osteotomy procedures.

SUMMARY

Certain embodiments of the disclosure concern radial saw blades and hub members that can be used to create osteotomies during orthopedic procedures remove bone material as the cut is made. In a representative embodiment, a saw blade comprises a main body including a first surface, a second surface on an opposite side of the main body from the first surface, a proximal edge portion, a distal edge portion, and first and second side portions extending between the proximal and distal edge portions. The proximal edge portion comprises a U-shaped recess extending distally from the proximal edge portion. The proximal edge portion is configured to be coupled to a rotatable hub such that the saw blade is held in a curved shape with the first surface defining an outer radius when the saw blade is coupled to the rotatable hub. The distal edge portion comprises a plurality of cutting teeth, and the saw blade has a thickness of from 0.005 inch to 0.018 inch.

In another representative embodiment, an assembly comprises a hub member including a hub portion and a curved coupling portion. The coupling portion is radially offset from the hub portion with respect to a longitudinal axis of the hub portion about which the hub member is configured to rotate. The coupling portion includes a slot defined in a distal surface of the coupling portion. The hub member further includes at least one opening defined in a proximal surface of the hub member, and the at least one opening is in fluid communication with the slot of the coupling portion. The assembly further comprises a blade received in the slot of the coupling portion. The blade includes at least one tab portion extending through the opening in the proximal surface of the hub member and folded over to engage the hub member.

In another representative embodiment, an assembly comprises a hub member including a hub portion and a curved coupling portion. The coupling portion is radially offset from the hub portion with respect to a longitudinal axis of the hub portion about which the hub member is configured to rotate. The coupling portion includes a first extension portion extending from a first side portion of the coupling portion, and a second extension portion extending from a second side portion of the coupling portion opposite the first side portion. The hub member further comprises a third extension portion extending from a central portion of the coupling portion, and a fourth extension portion extending from the central portion and radially offset from the third coupling portion such that the third and fourth extension portions are spaced apart from each other relative to the longitudinal axis of the hub portion. The assembly further comprises a blade coupled to the hub member such that the blade is situated on the first and second extension portions, and received between the third and fourth extension portions of the coupling portion. The blade includes a U-shaped recess. The assembly further includes a fastener extending through the third extension portion, the U-shaped recess of the blade, and the fourth extension portion to secure the blade to the hub member.

In another representative embodiment, an assembly comprises a hub member including a hub portion and a curved coupling portion, the coupling portion being radially offset from the hub portion with respect to a longitudinal axis of the hub portion about which the hub member is configured to rotate. The coupling portion comprises at least one extension portion configured to receive a blade. The assembly further comprises an elongated guide member couplable to the hub portion of the hub member and configured to extend along the longitudinal axis of the mounting portion.

In another aspect, the assembly further comprises a clamping member configured to clamp a blade between the clamping member and the at least one extension portion.

In another aspect, the the coupling portion includes an upper extension portion and three lower extension portions radially offset from the upper extension portion with respect to the longitudinal axis of the hub member such that a blade can be received between the upper extension portion and the lower extension portions.

In another aspect, at least one of the lower extension portions includes a post configured to be received in a corresponding opening defined in a blade when a blade is coupled to the coupling portion.

In another aspect, the hub portion of the hub member defines an opening, and the assembly further comprises a magnet disposed in the opening to magnetically engage the guide member.

In another aspect, the hub member includes a pair of arms extending between the hub portion of the hub member and the coupling portion of the hub member.

In another representative embodiment, a method comprises drilling a guide hole in a bone, and inserting a guide member of a hub assembly into the guide hole. The hub assembly comprises a hub member including a hub portion and a curved coupling portion. The coupling portion is radially offset from the hub portion with respect to a longitudinal axis of the hub portion about which the hub member is configured to rotate. The coupling portion comprises at least one extension portion on which a blade is received, and the guide member is coupled to the hub portion of the hub member such that the guide member extends along the longitudinal axis of the hub portion. The method further comprises cutting the bone with the blade.

In another aspect, the blade comprises a main body including a first surface and a second surface. The second surface is on an opposite side of the main body from the first surface, and the first surface defines an outer radius. The second surface comprises a cutting structure configured such that a radius of an arc swept by the cutting structure when the blade is rotated is substantially equal to the outer radius of the first surface.

In another representative embodiment, a saw blade comprises a main body including a first surface, a second surface on an opposite side of the main body from the first surface, a proximal edge portion, a distal edge portion, and first and second side portions extending between the proximal and distal edge portions. The proximal edge portion is configured to be coupled to a rotatable hub such that the saw blade is held in a curved shape with the first surface defining an outer radius when the saw blade is coupled to the rotatable hub. The distal edge portion comprises a plurality of cutting teeth, and the second surface comprises a cutting structure configured such that a radius of an arc swept by the cutting structure when the saw blade is rotated is substantially equal to the outer radius of the first surface.

In another aspect, the cutting structure comprises a plurality of projections.

In another aspect, the projections are rounded lobes.

In another aspect, the projections comprise cutting surfaces oriented in the direction of at least one of the side portions of the main body.

In another aspect, a distal edge of the cutting structure is proximally offset from the distal edge portion of the main body.

In another aspect, first and second side portions of the cutting structure are offset from the first and second side portions of the main body toward a longitudinal axis of the main body.

In another aspect, a thickness of the main body increases along at least a portion of a width dimension of the main body from the first side portion in a direction toward a longitudinal axis of the main body, and in a direction from the second side portion toward the longitudinal axis of the main body.

In another aspect, the cutting structure comprises a plurality of ridges extending along the second surface.

In another aspect, the heights of the apices of the ridges vary along the main body.

In another aspect, the cutting teeth extend from respective ridges of the cutting structure.

In another aspect, width dimensions of respective base portions of the cutting teeth vary along a width dimension of the saw blade.

In another aspect, the width dimensions of base portions of cutting teeth adjacent the first and second side portions are greater than the width dimensions of cutting teeth adjacent a longitudinal axis of the saw blade.

The foregoing and other objects, features, and advantages of the disclosed technology will become more apparent from the following detailed description, which proceeds with reference to the accompanying figures.

BRIEF DESCRIPTION OF THE DRAWINGS

FIGS. 6A and 6B illustrate the effects of saw blade thickness on an osteotomy site.

FIGS. 7A-7C illustrate the effects of saw blade thickness on the respective radii of the cut bone surface and the surface of the bone segment.

FIGS. 11-13 illustrate another embodiment of a radial saw blade with a varying thickness and a cutting structure on the radially inward surface of the blade.

FIGS. 14A and 14B illustrate an embodiment of the cutting structure of the blade of FIGS. 11-13 in greater detail.

FIG. 15 illustrates another embodiment of the blade of FIGS. 11-13.

DETAILED DESCRIPTION

Figure 1:
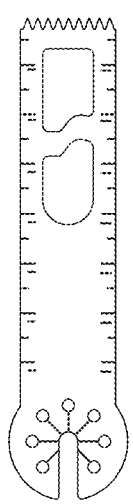
FIGS. 1-3 are representative examples of saw blades that can be used in the osteotomy procedures described herein.
Figure 2:
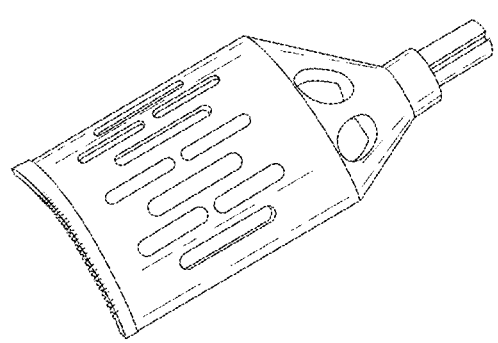
Figure 3:
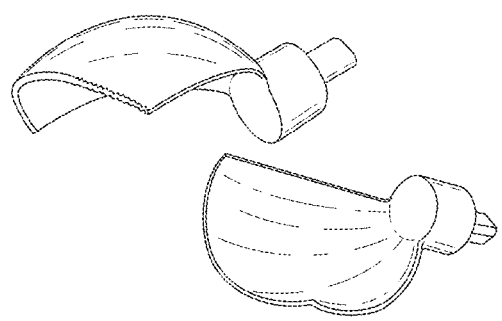

In human and animal orthopedics, various saw blades are available to make osteotomies in bone. Straight osteotomies, radial osteotomies, and spherical osteotomies can be created at specific locations in long bones to achieve realignment of a bone segment to the overall limb axis for improved biomechanics. Representative examples of a flat saw blade, a radial saw blade, and a spherical or dome saw blade are shown in FIGS. 1-3, respectively.

There are multiple physiological problems associated with long bones that can affect limb biomechanics, which can occur as a result of trauma (e.g., bone fractures that heal in a misaligned position), or birth defects. Surgical methods of re-establishing appropriate biomechanics of a limb can include repositioning proximal and distal bone segments to correct alignment issues. There are clinical examples for many long bones (e.g., femur, tibia, humerus, radius, ulna, etc.), which can be managed through corrective osteotomies to restore improved limb function in which a portion of the bone (referred to herein as a "bone segment" or "excised portion") is excised from the remainder of the bone, and reattached to the bone in a specified position and/or orientation to address the subject pathology. With reference to the femur, there are proximal and distal corrective osteotomies that can address different biomechanical alignment issues.

Figure 4A:
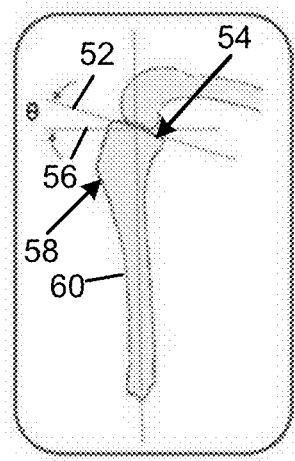
FIGS. 4A-4C illustrate a representative tibial plateau leveling osteotomy (TPLO) procedure.
Figure 4B:
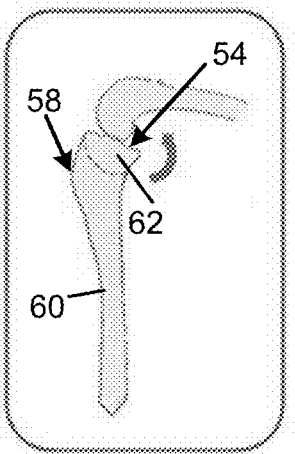
Figure 4C:
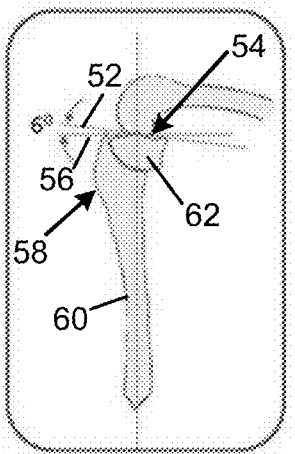

For example, in veterinary medicine, a tibial plateau leveling osteotomy (TPLO) can be performed to re-position the tibial plateau to, for example, function as a buttress to resist certain physiological movements or address rupture of the anterior (cranial) cruciate ligament. FIGS. 4A-4C illustrate a representative example of a TPLO procedure. FIG. 4A illustrates a normal angle θ between a plane 52 defined by the tibial plateau 54 and a horizontal reference plane 56. In certain circumstances, it can be beneficial to rotate the plane 52 of the tibial plateau 54 to reduce the angle between the tibial plateau and the reference plane 56. This can be accomplished by creating a radial cut in a proximal portion 58 of the tibia 60 and rotating the excised portion 62 such that the angle between the tibial plateau 54 and the horizontal reference plane 56 is lowered (e.g., to about 6 degrees in some embodiments), as shown in FIGS. 4B and 4C.

Figure 5A:
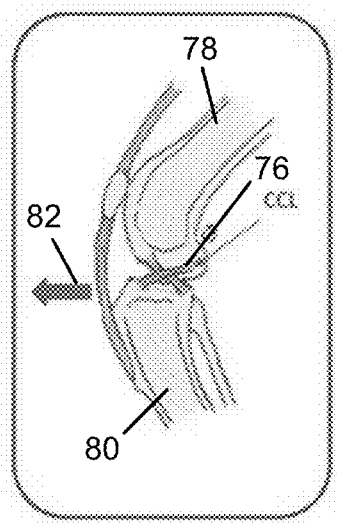
FIGS. 5A-5C illustrate a representative repair of a ruptured cranial cruciate ligament by performing a TPLO.
Figure 5B:
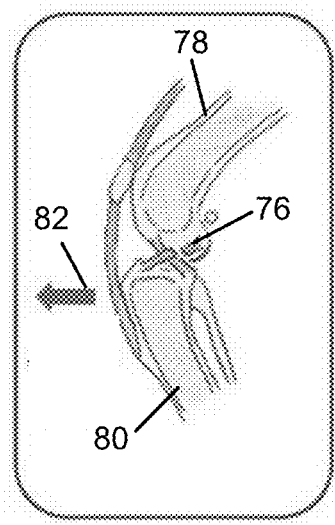
Figure 5C:
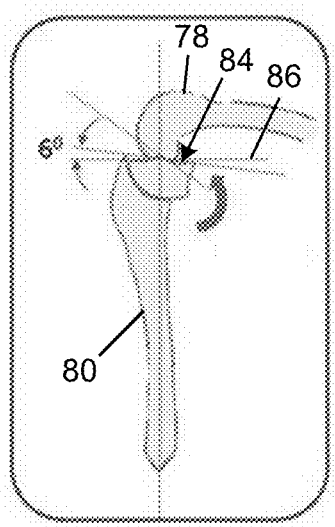

A TPLO procedure may be performed to compensate for ruptures of the cranial cruciate ligament (for example, in dogs). A representative example of a TPLO to repair a ruptured cranial cruciate ligament is illustrated in FIGS. 5A-5C. As illustrated in FIG. 5A, the cranial cruciate ligament 76 can extend between the femur 78 and the tibia 80, and can resist advancement of the tibia in the direction indicated by arrow 82 due to force applied to the tibia by the femur. FIG. 5B illustrates forward advancement of the tibia 80 in the direction of arrow 82 due to rupture of the cranial cruciate ligament 76. In a typical example, an osteotomy using any of the saw blades disclosed herein can be made in the lateral plane on the medial side of the tibia 80 to reduce the angle θ (FIG. 4A) of the tibial plateau 84 with respect to a horizontal reference plane 86, as illustrated in FIG. 5C. This can create a mechanical abutment in the caudal aspect of the knee, assisting the soft tissues in preventing the femur from sliding off the back of the tibia, mitigating the effects of a non-functional cranial cruciate ligament.

In certain configurations, radial saw blades used for TPLO procedures can be one-piece constructs, or assemblies of two or more separate components, such as a hub and detachable blade. In certain examples, the blade oscillates along an arc having a radius substantially equal to a radius of the blade. For example, the blade may move through an angle of about ±8 degrees with a frequency of about 500 Hz to about 1,000 Hz. Blades may be used for multiple surgical procedures, and can be discarded or sharpened when, for example, the blade fails to perform adequately intraoperatively. Some indications of blade failure include inadequate advancement of the blade through the bone, burning of the bone, and/or breakage of the blade. In some embodiments, blades may be used about 20 times, or as many as 100 times. However, in certain circumstances, a blade may begin to generate excessive heat after only a few uses. When temperatures of over 47° C. are generated at the bone interface, necrosis may occur. Necrosis at the osteotomy interface can delay healing, and can increase the risk of non-union of the bone and the excised bone segment, requiring surgical intervention. In some cases, non-union of the bone and the excised portion at the osteotomy interface can result in undesirable motion (e.g., micromotion) of the plate-screw reconstruction of the TPLO, which may lead to fatigue failure of the implants.

Additionally, a radial saw blade may create a mismatch between the radius of the cut surface of the bone and the radius of the excised portion at the osteotomy interface. This concept is illustrated in FIGS. 6A and 6B, wherein a thickness t (FIG. 6B) of a radial saw blade 10 results in a gap 11 between a bone 12 and an excised portion or bone segment 14 of the bone (e.g., before complete excision of the bone segment 14). The gap 11 has a width w that corresponds to the thickness t of the saw blade, and can result from, for example, removal or ablation of bone material by the saw blade 10 as the blade advances through the bone.

The resulting osteotomy surface 16 on the bone 12 and the corresponding osteotomy surface 18 on the excised bone segment 14 can have different radii. Referring to FIG. 7A, an outer surface 20 of the saw blade 10 defines a circular path 22. In certain examples, the outer surface 20 of the saw blade creates the osteotomy surface 16 on the bone 12 (FIG. 6A) as the blade advances through the bone. The path 22 of the outer surface 20 and, thereby, the osteotomy surface 18, can have a radius ii. Meanwhile, an inner surface 24 of the blade can define a circular path 26 having a radius $r_1$. The inner surface 24 creates the osteotomy surface 18 of the excised bone segment 14 and, thus, the osteotomy surface 18 has a radius equal to $r_2$. The radius $r_1$ can be greater than the radius $r_2$, and the difference between the radii $r_1$ and $r_2$ can be a function of the thickness t of the saw blade 10. Thus, thicker saw blades can result in wider gaps (e.g., more bone removed), which must be closed and/or compressed for healing. Thicker saw blades can also result in greater mismatch between the radii of the osteotomy surfaces. This is shown in FIGS. 7A-7C, which illustrate saw blades with increasing thickness and the resulting mismatch in radii between the osteotomy surfaces of the bone 12 and the excised portion 14. FIG. 7A illustrates a relatively thin saw blade with a thickness of, for example, about 0.25 mm, FIG. 7B illustrates a blade of medium thickness (e.g., 0.65 mm), and FIG. 7C illustrates a relatively thick blade (e.g., a thickness of 1 mm). The mismatches created by increased saw blade thickness can contribute to instability and undesirable motion (e.g., rocking) when the osteotomy surfaces are mated, which can contribute to increased recovery time and potential complications (e.g., non-union of the osteotomy surfaces or implant failures).

In some cases, freehand control of the saw blade and the power saw may also contribute to inaccuracy in the path of the osteotomy. Generally, the cut is made perpendicular to the long axis of the bone. Existing guide tools can be cumbersome, and extensive setup is often required. Therefore, cuts may be made without guiding instruments, which can result in inaccuracies in the plane of the cut and the cut site.

Figure 8:
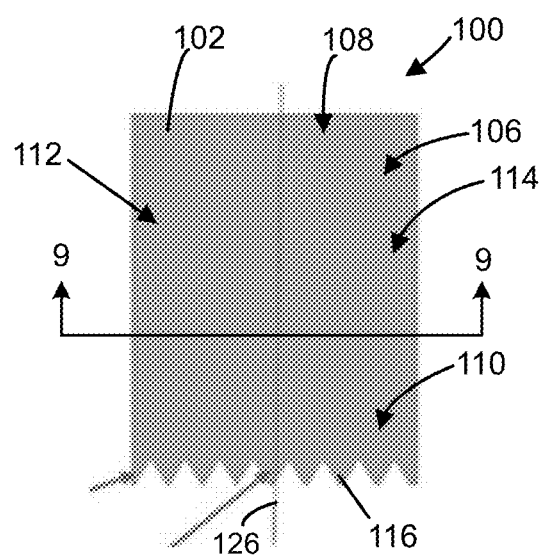
FIGS. 8-10 illustrate a representative embodiment of a radial saw blade with a thickness that varies along the cross-section of the blade.
Figure 9:
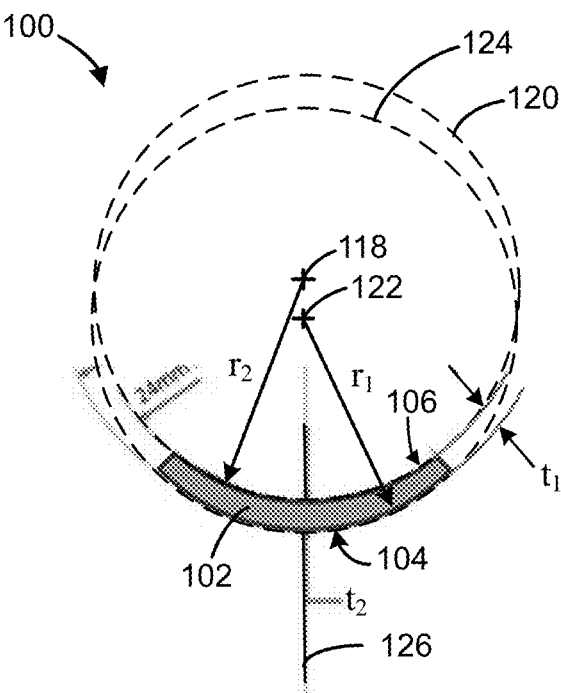

FIGS. 8 and 9 illustrate a representative embodiment of a radial saw blade 100 configured such that the radius of the inner surface is equal to or substantially equal to the radius of the outer surface. The saw blade 100 can include a main body 102 having first and second surfaces 104, 106 (see FIG. 9), a proximal edge portion 108, and a distal edge portion 110. First and second side portions 112, 114 extend between the proximal and distal edge portions 108, 110. The distal edge portion 110 comprises a plurality of cutting teeth 116.

Figure 10:
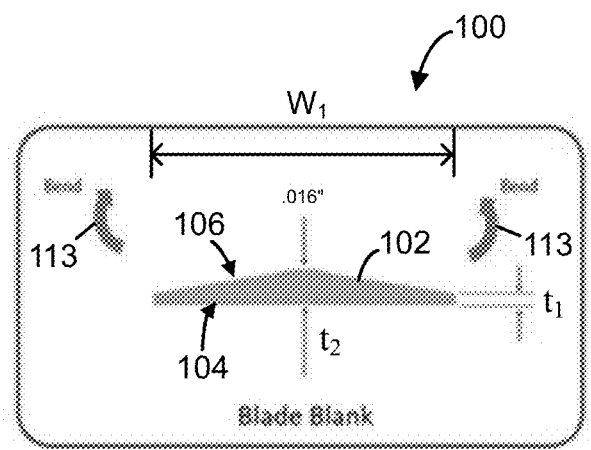

FIG. 9 illustrates a cross-sectional view of the saw blade 100 taken along line 9-9 of FIG. 8. As illustrated in FIG. 9, the main body 102 of the saw blade can have a curved shape (e.g., when coupled to a hub assembly, such as the hub assembly described below) such that the first surface 104 defines an outer radius $r_1$ and the second surface 106 defines an inner radius $r_2$. A longitudinal axis 126 of the blade is shown extending along a mid-plane of the blade. FIG. 10 illustrates a saw blade "blank" before the body of the blade is bent into a curved shape. As illustrated in FIG. 10, the thickness of the saw blade can vary along a width dimension $W_1$ of the blade. For example, in the illustrated embodiment, the thickness of the saw blade can increase from a first thickness $t_1$ at the side portions 112, 114 to a second thickness $t_2$ at or near the midpoint of the width dimension $W_1$ to form an apex. In this manner, the saw blade has a triangular cross-sectional shape. This variation in thickness from the outer edges to the center of the saw blade causes the center 118 (FIG. 9) of a circle 120 defined by the second surface 106 to be offset from a center 122 of a circle 124 defined by the first surface 104 along a longitudinal axis 126. As shown in FIG. 9, this allows the radius $r_2$ of the second surface 106 to be equal to or substantially equal to the radius $r_1$ of the first surface 104. Stated differently, the radius $r_2$ of an arc (e.g., along circular path 120) swept by the second surface 106 is equal to or substantially equal to the radius $r_1$ of the first surface 104. As used herein, "substantially equal" means that the radius $r_2$ can be 80% or more of the radius $r_1$, 90% or more of the radius $r_1$, 95% or more of the radius $r_1$, or 100% of the radius $r_1$. In this manner, the radius of a bone surface cut by the first surface 104 will be the same or nearly the same as the radius of a corresponding surface of a bone segment cut from the bone by the second surface 106 of the blade.

In some embodiments, the thickness $t_2$ can be from about 105% to about 200% of the thickness $t_1$. In some embodiments, the thickness $t_2$ can be, for example, about 120% to about 150% of the thickness $t_1$. In some embodiments, the thickness $t_2$ can be about 130% of the thickness $t_1$. In a representative embodiment, the thickness $t_1$ can be 0.012 inch and the thickness $t_2$ can be about 0.016 inch, such that the thickness $t_2$ is about 133% of the thickness $t_1$.

Prior to use, the blade can be bent into a curved shape in the manner indicated by arrows 113. The blade can be curved to achieve a variety of radii, which can correspond to the size of the animal or the particular bone upon which an osteotomy is to be performed. Thus, in some examples, the radii $r_1$ and $r_2$ can be about 18 mm, 20 mm, 24 mm, etc. In some embodiments, the thickness of the blade can range from about 0.005 inch to about 0.020 inch. Making the blade thickness within this range can, for example, improve the speed of the cut, generate less heat, and reduce the gap at the bone interface while maintaining strength and rigidity of the blade.

FIGS. 11-13 illustrate another embodiment of the saw blade 100 wherein the second surface 106 includes a cutting structure 128. In the illustrated embodiment, the cutting structure 128 has a length L and a width dimension $W_2$, and is proximally offset from the distal edge of the blade (e.g., from the tips of the teeth 116) by a distance d. The portion of the blade defined between the tips of the teeth 116 and the distal edge of the cutting structure 128 is denoted portion 130. In one exemplary embodiment, the distance d can be about 4 mm, although it should be understood that the cutting structure 128 can be offset from the distal edge of the blade by any suitable distance, or can extend all the way to the distal edge of the blade, as desired. In the illustrated embodiment, the width dimension $W_2$ of the cutting structure 128 is substantially equal to the width dimension $W_1$ (FIG. 10) of the blade. However, in other embodiments the cutting structure need not extend across the entire width dimension $W_1$ of the blade.

Referring to FIG. 12, the distal portion 130 of the blade (including the teeth 116) can have a thickness of $t_1$ across the full width of the blade. Referring to FIG. 13, the thickness of the portion of the blade including the cutting structure 128 can vary along the width dimension $W_1$ from $t_1$ at the side portions 112, 114 to $t_2$ at or near the midpoint of the blade, similar to the embodiment of FIG. 8. In this manner, a radius of an arc swept by the cutting structure 28 can be equal to or substantially equal to the radius of the first surface 104 such that osteotomy surfaces produced by the cutting structure 128 and the first surface 104 have equal or substantially equal radii. In some embodiments, the thickness of the portion of the blade including the cutting structure 128 may increase gradually with increasing distance from the respective side portions. In other embodiments, the thickness may increase over a relatively short distance, or in a step. For example, FIG. 15 illustrates another embodiment of the blade 100 in which the thickness of the main body coinciding with the cutting structure 128 increases in a step from $t_1$ to $t_2$ to form a raised platform 138 having a thickness $t_2$.

In certain examples, the cutting structure 128 can be a roughened or textured portion of the second surface 106 configured to cut or abrade material from a bone in the manner of a file. For example, with reference to FIGS. 14A and 14B, the cutting structure 128 can comprise a plurality of protrusions 132 extending from the second surface 106. In one representative example, the protrusions can have cylindrical bases, heights of about 0.18 mm, and diameters of about 1.5 mm. In other examples, the protrusions can have any suitable height and any suitable shape (e.g., a triangular shape, an oval shape, pyramidal shape, etc.), or combinations of shapes. In some examples, the protrusions 132 can be formed by chemical etching of the features onto the surface of the blade.

In the illustrated configuration, the protrusions 132 can have cutting surfaces or faces 134. In some embodiments, the cutting surfaces 134 can be substantially planar, and can be oriented toward either the first side portion 112 or the second side portion 114. In this manner, the cutting surfaces 134 can be substantially perpendicular to the direction of travel of the blade when the blade is in use. For example, when used in combination with an oscillating blade driver, the protrusions 132 oriented toward the first side portion 112 can be incident upon a bone being cut when the blade is rotated clockwise, and the protrusions 132 oriented toward the second side portion 114 can be incident upon the bone when the blade is rotated counterclockwise. This allows the protrusions 132 of the cutting structure 128 to remove bone in both directions as the saw blade oscillates.

Figure 16:
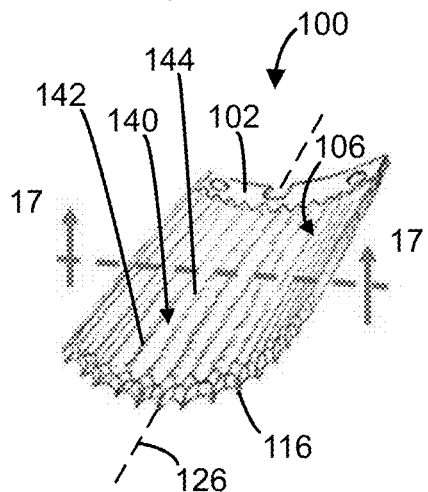
FIGS. 16 and 17 illustrate another embodiment of a radial saw blade where the radially inward surface of the blade has a cutting structure comprising a plurality of longitudinally extending ridges.
Figure 17:
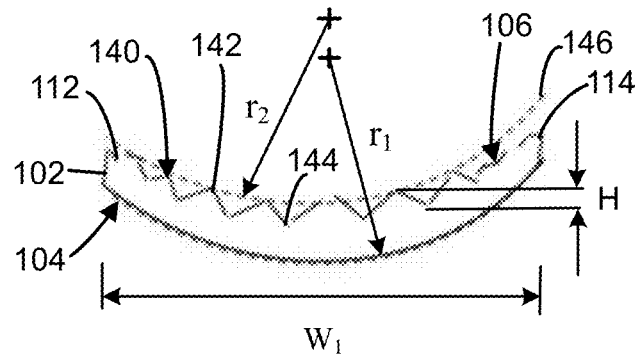

FIGS. 16 and 17 illustrate another embodiment of the blade 100 wherein the second surface 106 includes a cutting structure comprising a plurality of ridges 140. In the illustrated embodiment, the ridges 140 extend lengthwise along the second surface parallel to the longitudinal axis 126 such that the second surface defines a plurality of peaks or apices 142 and valleys 144. The ridges 140 can be aligned with the teeth 116 such that each ridge is aligned (e.g., coaxially aligned) with a corresponding tooth. Referring to FIG. 17, the height dimension H of the ridges 140 can vary along the width $W_1$ of the blade. For example, in the illustrated embodiment, the heights H of the ridges 140 located at or near the midpoint of the blade can be higher than the heights of the ridges 140 located closer to the side portions 112, 114. In certain examples, the teeth 116 can also extend from the apices 142 of the ridges 140, through the thickness of the blade, to the first surface 104. Thus, the height of the teeth 116 (e.g., at the base of the teeth) can be the same as the heights H of the corresponding ridges 140 from which they extend. By varying the tooth and ridge heights along the width of the second surface 106, a radius $r_2$ of a curve 146 (e.g., a circle) defined by the apices 142 of the ridges 140 can be equal to or substantially equal to a radius $r_1$ of the first surface 104, as illustrated in FIG. 17. In this manner, the teeth 116 and/or the ridges 140 can cut a bone such that the osteotomy surfaces created on both sides of the blade have equal or substantially equal radii. The channels defined between the ridges 140 can also serve as conduits for irrigation fluid (e.g., saline solution), which can improve heat dissipation at the distal end of the blade, helping to avoid overheating during an osteotomy procedure and associated tissue necrosis.

In alternative embodiments, the ridges 140 can extend at an angle to the longitudinal axis 126 of the blade, such as perpendicular to the longitudinal axis of the blade. In some embodiments, the angles of the sides of the teeth 116 and, hence, the width of the bases of the teeth, can be the same or different along the width of the blade, as desired.

Figure 18:
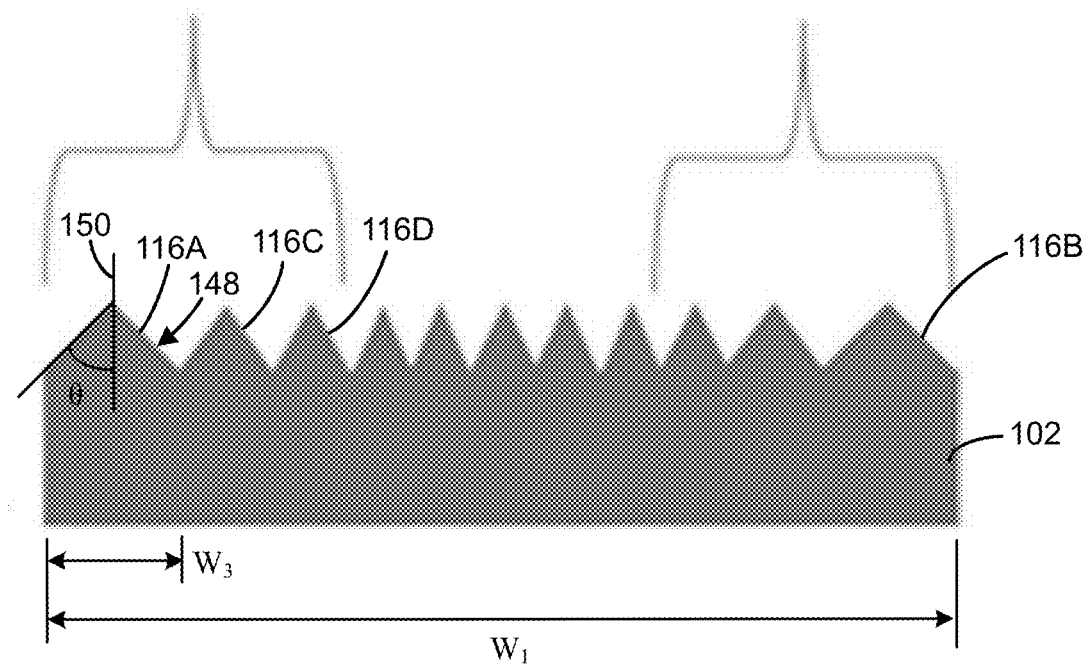
FIG. 18 illustrates another embodiment of a radial saw blade wherein angles formed by the sides of the cutting teeth vary along the width of the blade.

FIG. 18 illustrates another embodiment of the blade 100 in which the angle θ formed between the sides 148 of the teeth 116 and a reference axis (e.g., axis 150 extending through the apex of the tooth) varies along the width $W_1$ of the blade. Stated differently, the angles of the sides 148 of the teeth 116 can be varied such that a width dimension $W_3$ of the teeth 116 varies along the width $W_1$ of the blade. For example, in the illustrated embodiment, the teeth 116A, 116B nearest the edges of the side portions 114, 116 (e.g., at the leading and/or trailing edges of the blade when in use) can have relatively larger angles θ than other teeth. Thus, the widths $W_3$ of the bases of teeth 116A, 116B are greater than the widths $W_3$ of the bases of the teeth located at near the midpoint of the blade. This results in greater strength of the teeth 116A, 116B, allowing them to withstand the higher loading attendant to being located at the leading edge of the blade without significant deformation.

In the illustrated embodiment, the angle θ of the teeth 116A, 116B can be from about 30 degrees to about 80 degrees. In an exemplary embodiment, the angle θ of the teeth 116A, 116B can be about 45 degrees. In the illustrated configuration, the angle θ of the teeth can gradually decrease in a direction toward the midpoint of the blade. For example, in one representative embodiment, with reference to the tooth 116A for purposes of illustration, the angle θ of tooth 116A can be about 45 degrees, and the angles of the next two teeth 116C and 116D in a direction toward the midpoint of the blade can be about 40 degrees, and about 35 degrees, respectively. The teeth on the opposite side of the blade can have a similar configuration. Meanwhile, the teeth near the midpoint of the blade can have an angle θ of, for example, about 30 degrees, although other configurations are possible. In other embodiments, the teeth 116 at or near the midpoint of the blade can be thicker than the teeth near the side portions 112, 114, as illustrated in FIG. 17.

Figure 19:
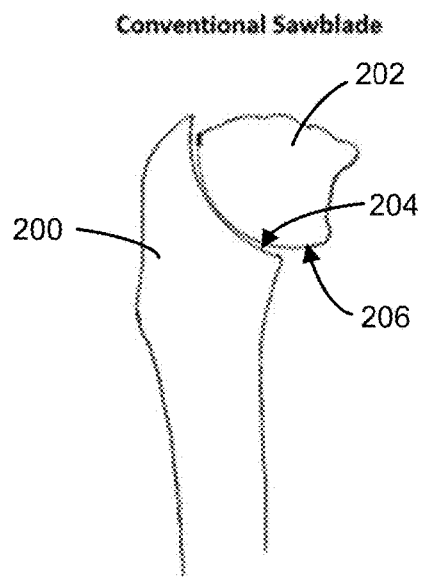
FIG. 19 is a side elevation view of a tibia illustrating the contours of an osteotomy performed with a conventional radial saw blade.
Figure 20:
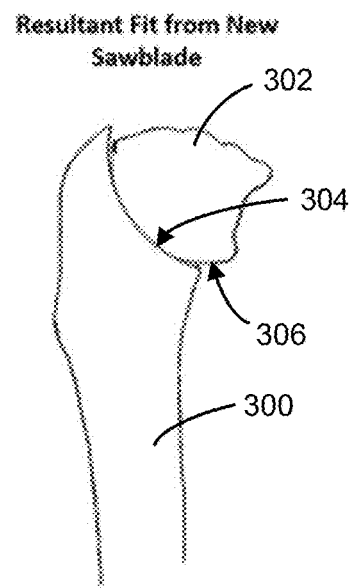
FIG. 20 is a side elevation view of a tibia illustrating the contours of an osteotomy performed with the saw blade of FIGS. 11-13.
Figure 21:
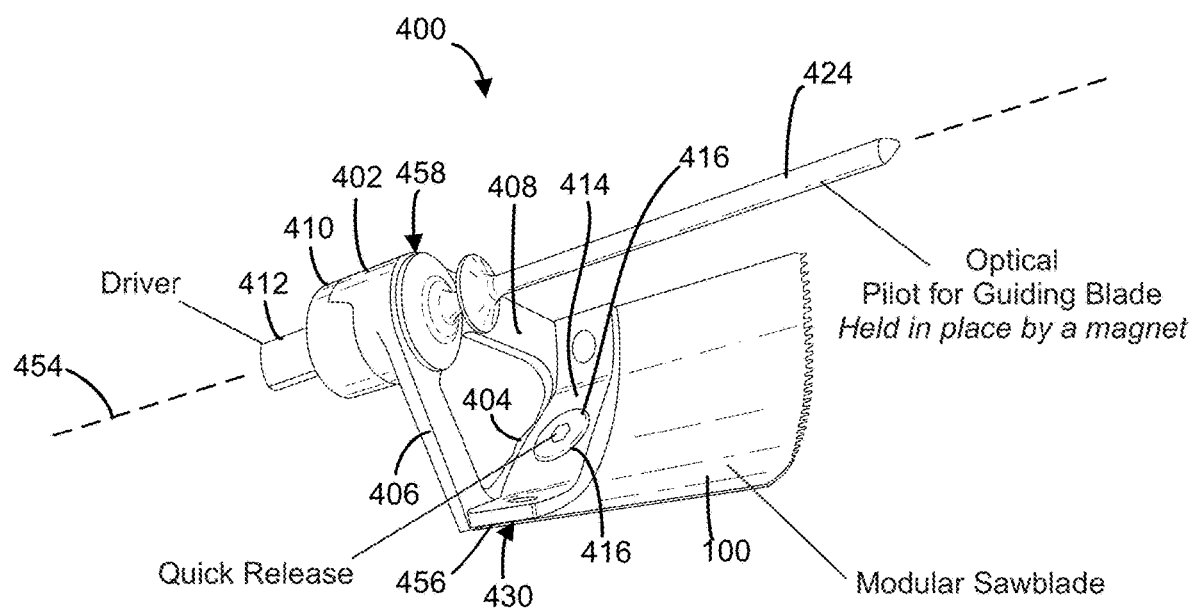
FIG. 21 is a perspective view of a representative embodiment of a hub assembly.
Figure 22:
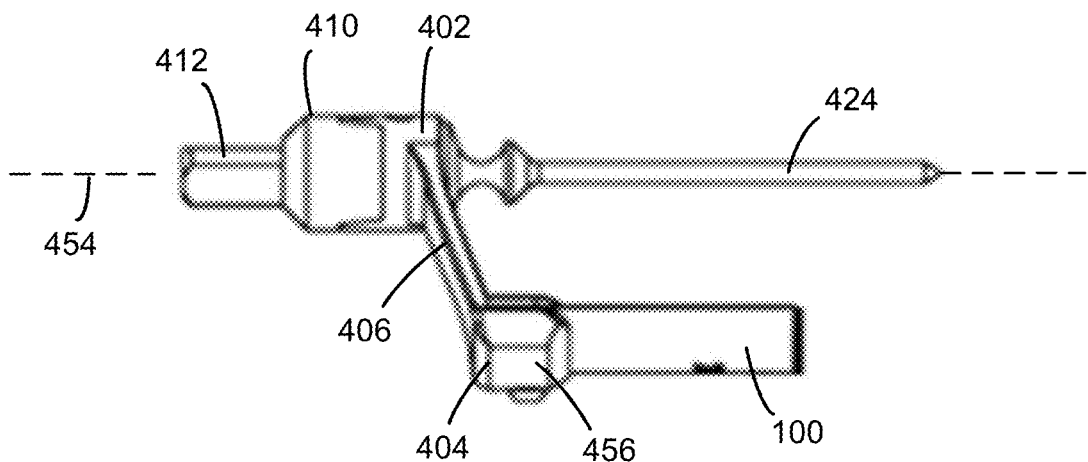
FIG. 22 is a side elevation view of the hub assembly of FIG. 21
Figure 23:
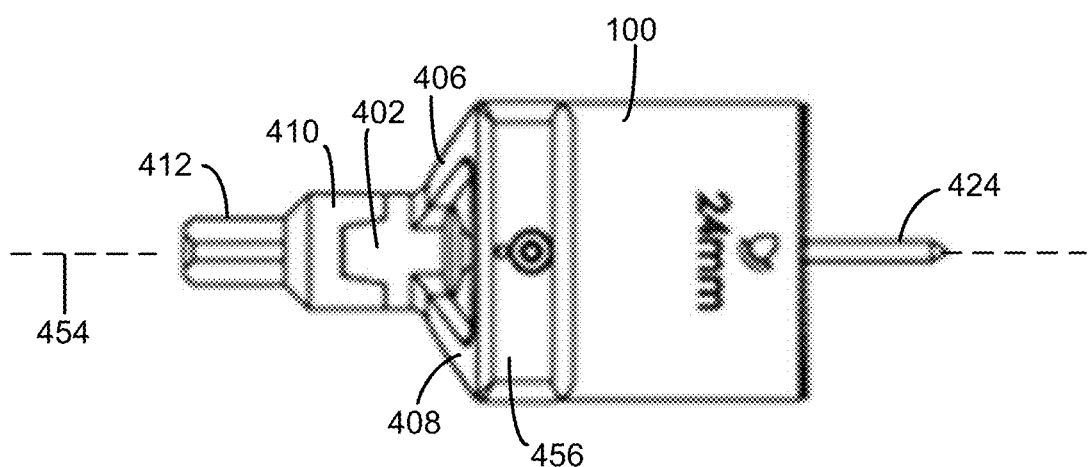
FIG. 23 is a bottom plan view of the hub assembly of FIG. 21.

FIGS. 19 and 20 illustrate the fit between a bone and a bone segment cut with the blade configurations described herein (FIG. 20) as compared to a conventional radial saw blade (FIG. 19). As shown in FIG. 19, there is a significant mismatch between the radius of a surface 204 of the bone 200 and a surface 206 of the bone segment 202 cut with a conventional radial saw blade, resulting in a relatively small contact area, and relatively large gaps between the bone 200 and the bone segment 202 at the ends of the radial cut. In contrast, FIG. 20 illustrates the fit between a bone 300 and a bone segment 302 cut from the bone 300 using a radial saw blade with the cutting structure of FIGS. 11-13. As shown in FIG. 20, the radius of the surface 304 of the bone 300 closely matches the radius of the surface 306 of the bone segment 302, resulting in a relatively larger area of contact between the bone and the bone segment, and relatively smaller gaps between the bone and the bone segment at the ends of the radial cut.

FIGS. 21-24 illustrate a hub assembly 400 configured to receive a radial saw blade 100, which can be configured as any of the blade embodiments described herein. The hub assembly can include a hub member 402 including an upper portion configured as a hub portion 458 and a lower portion configured as a support member 404 (also referred to as a coupling portion). The support member 404 can be coupled to the hub 402 and radially offset from a longitudinal axis 454 of the hub by a pair of arms 406, 408. In the illustrated embodiment, the longitudinal axis 454 extends through the hub portion 458. The arms 406, 408 can be angled toward one another such that the hub member 402 has a generally triangular shape. The support member 404 can be curved, and can include a curved cradle or extension portion 456 extending from the support member in a direction parallel to the longitudinal axis 454. The hub portion 458 of the hub 402 can be releasably coupled to a chuck 410 including a drive shaft 412, which can be received by a blade driver (e.g., a BJ2100 handpiece available from Shanghai Bojin Medical Instrument Co., Ltd.). Rotational motion imparted to the drive shaft 412 by the blade driver results in rotational motion (e.g., oscillating rotational motion) of the hub 402 and, thus, of the blade 100, about the longitudinal axis 454.

Figure 24:
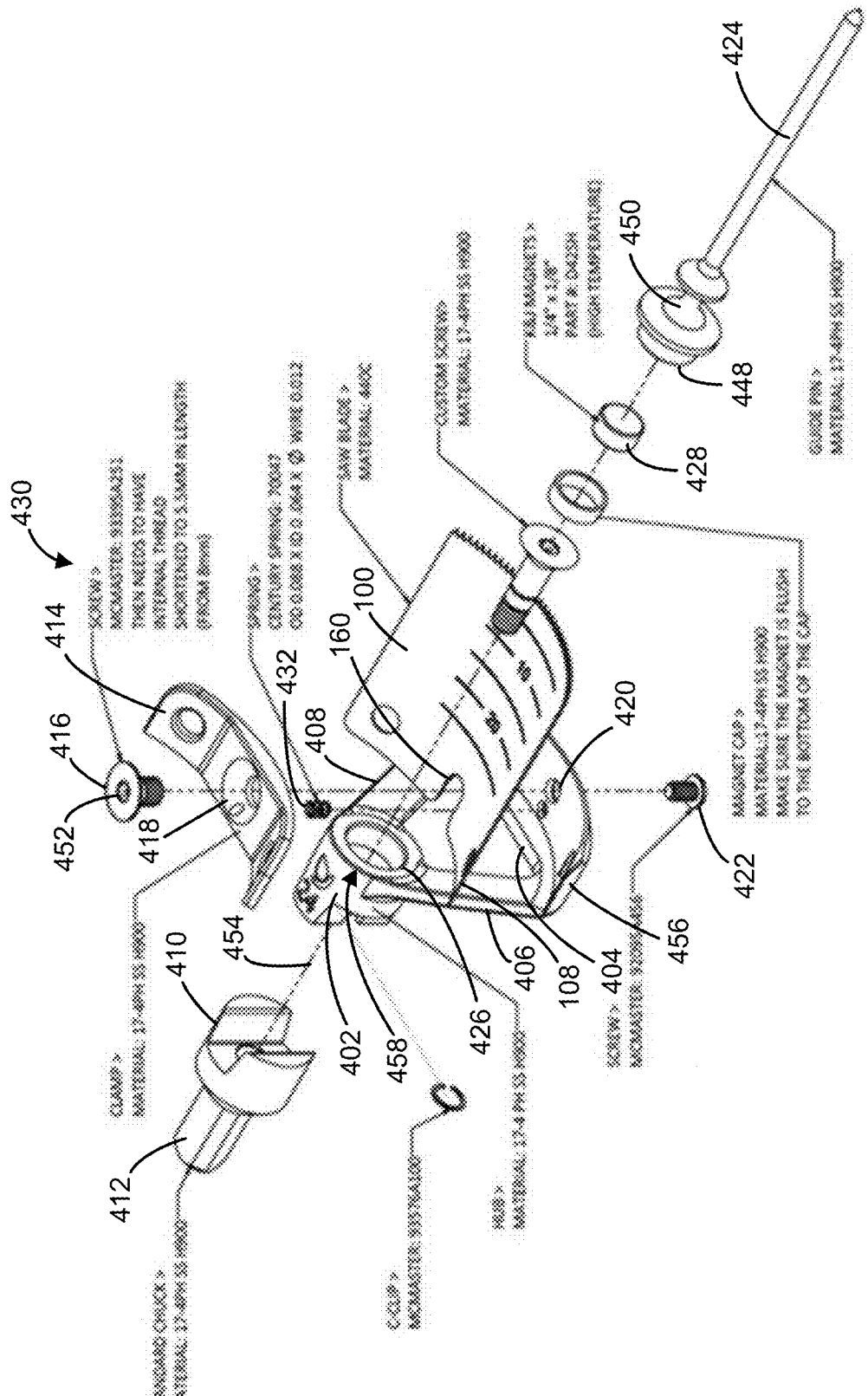
FIG. 24 is an exploded view of the hub assembly of FIG. 21.

In the illustrated embodiment, the blade 100 can be coupled to the hub assembly by a blade coupling assembly generally indicated at 430. Referring to FIG. 24, the blade coupling assembly 430 can include a clamp member 414 and a fastener 416 configured to be inserted into an opening 420 defined in the extension portion 456. In the illustrated embodiment, the fastener 416 can have external threads on the shank, and can also define an opening 452 extending at least partially through the length of the fastener that can include internal threads. The blade 100 can define a U-shaped recess 160 at the proximal edge portion 108 and extending distally from the proximal edge portion, and the clamp member 414 can define an opening 418. When the blade 100 is positioned on the extension portion 456, the clamp member 414 can be placed over the blade, and the fastener 416 can be inserted through the opening 418 in the clamp member, through the recess 160, and through the opening 420 in the extension portion 456. A second fastener 422 can then be inserted into the opening 452 in the fastener 416 such that the threads of the fastener 422 engage the internal threads of the fastener 416 to secure the blade 100 to the hub 402. The extension portion 456 (and the support member 404) can be curved such that the blade 100 achieves a selected degree of curvature when secured to the extension portion. The blade 100 can be quickly and easily released from the hub by removing the fastener 416.

In the illustrated embodiment, the blade coupling assembly 430 can also include a spring 432 positioned between the extension portion 456 and the clamp member 414. The spring 432 can be configured to urge the clamp member 414 upwardly and away from the blade 100 when the fastener 416 is loosened to facilitate removal of the blade from the hub assembly.

The hub assembly 400 can also include a guide member 424. The guide member 424 can be received in an opening 426 defined in the hub portion 458 of the hub 402 such that the guide member is coaxially aligned with the drive shaft 412. In the illustrated configuration, a magnet 428 can be located in the opening 426 to magnetically engage a corresponding magnet 448 on the proximal end of the guide member 424 to retain the guide member in the opening 426. This can allow the guide member 424 to be easily attached to the hub assembly, or removed if a freehand cut is desired. In certain examples, a guide hole can be drilled into a bone to be cut, and the guide member 424 can be inserted into the guide hole when the bone is cut with the blade 100 to reduce or prevent wandering or misalignment of the blade when performing an osteotomy. In the illustrated embodiment, the guide member 424 can also include a grip portion 450 to facilitate attachment and removal of the guide member from the hub assembly.

Figure 25:
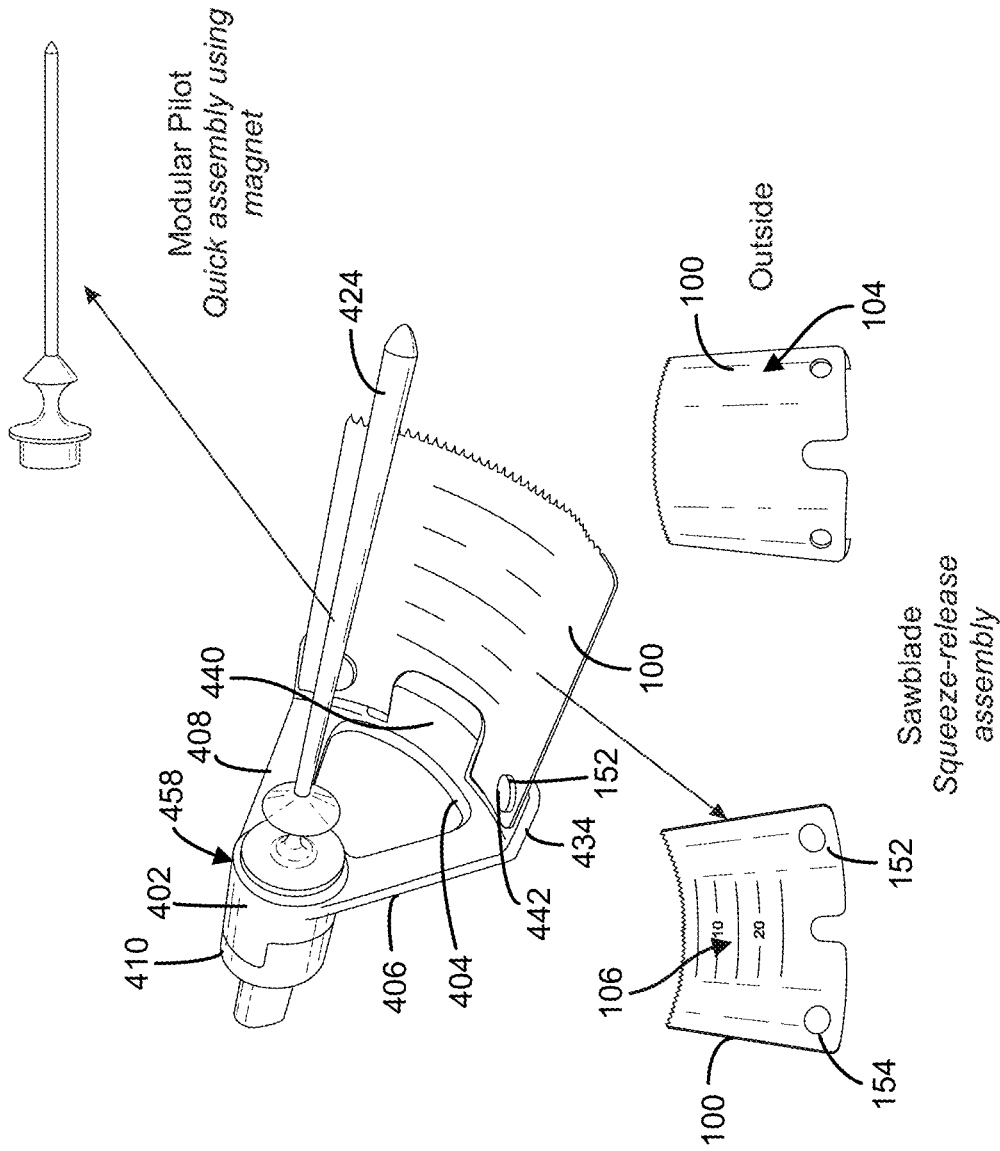
FIGS. 25A and 25B are perspective views of another embodiment of a hub assembly.
Figure 26:
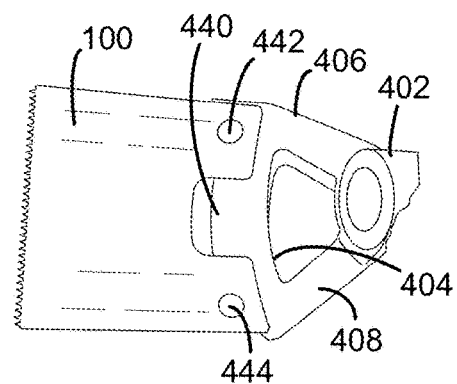
FIG. 26 is a top plan view of the hub assembly of FIGS. 25A and 25B.
Figure 27:
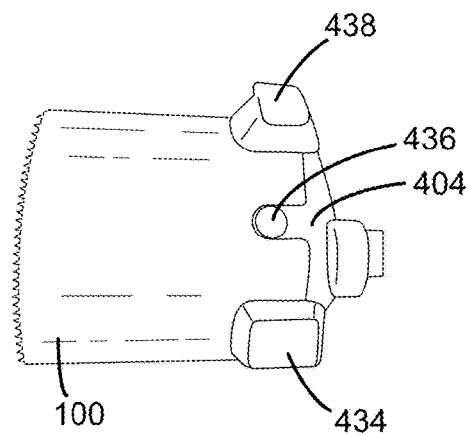
FIG. 27 is a bottom plan view of the hub assembly of FIGS. 25A and 25B.

FIGS. 25A, 25B, 26, and 27 illustrate another embodiment of the hub assembly 400 in which the blade coupling assembly 430 does not require any tools in order to secure or remove a blade from the hub. FIG. 25A shows the hub member 402 and the chuck 410 without the blade attached. In the illustrated configuration, the support member 404 (e.g., the lower portion of the hub member 402) includes three lower extension portions 434, 436 (see FIG. 27), and 438 spaced apart from one another along the length of the support member. An upper extension portion 440 extends over the lower extension portion 436. In the illustrated embodiment, the extension portions 436 and 440 extend from a central portion of the support member 404. The extension portion 434 includes a post 442, and the extension portion 438 includes a post 444. The blade 100 can define two openings 152, 154 corresponding to the posts 442, 444. As shown in FIG. 25B, the blade 100 can be inserted between the extension portion 436 and the extension portion 440, and the posts 442, 444 can be received in the respective openings 152, 154 of the blade to secure the blade to the hub assembly. In some embodiments, the support member 404 can have a smaller radius of curvature than the blade when the blade is in an unconstrained state. In this manner, the blade can be urged to conform to the smaller radius of the support member 404 when coupled to the support member, helping to keep the blade secured to the hub assembly.

Figure 28:
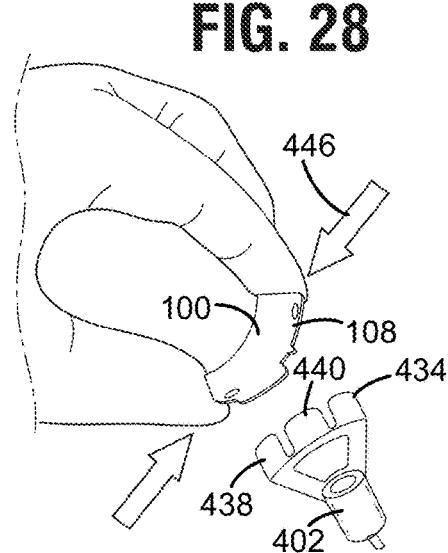
FIGS. 28 and 29 illustrate the process of securing a radial saw blade to the hub assembly of FIGS. 25A and 25B.
Figure 29:
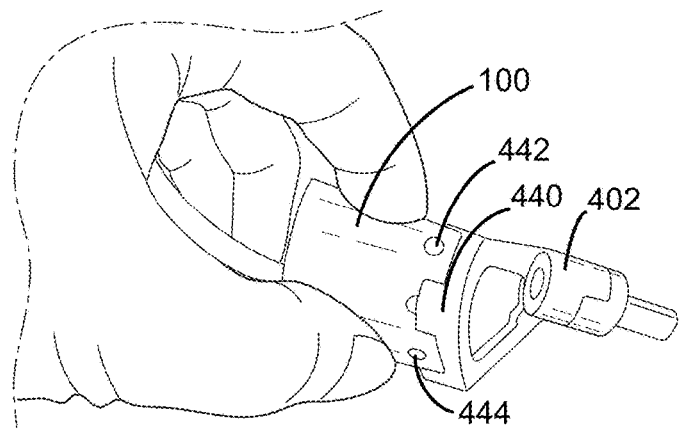

FIGS. 28 and 29 illustrate a method of coupling the blade 100 to the hub assembly 400 of FIGS. 25A-27. In a representative embodiment, a user can squeeze the blade 100 such that the blade radially deforms to a smaller radius of curvature in the manner of arrows 446. The proximal edge portion 108 can then be inserted between the extension portions 436 and 440 such that the posts 442, 444 are aligned with the openings 152, 154. The user can then release the blade such that the posts 442, 444 are received in the openings 152, 154 and the blade is secured to the hub assembly. This configuration allows quick coupling and removal of blades during operation without the use of tools if, for example, a blade needs to be replaced during an osteotomy procedure. It should also be understood that in alternative embodiments, the hub member 402 need not include arms, but can be a solid member including the support member 404 offset from the hub member 402 in the manner of FIG. 6B.

Figure 30:
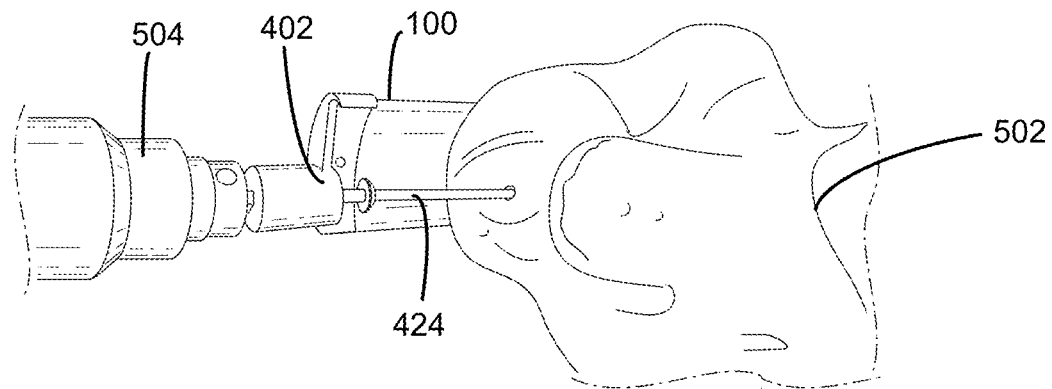
FIG. 30 is a perspective view illustrating a test of the radial saw blade of FIGS. 11-13.

FIG. 30 illustrates a test performed with a blade similar to the blade 100 of FIG. 11 in a bovine femur 502. The blade was made from 440A stainless steel with a radius of 24 mm (when secured to the blade driver) and a thickness of 0.012 inch at the edge portions. The blade was heat treated to achieve a Rockwell hardness of about RC 55. The blade 100 was coupled to a blade driver 504. First, a 2.5 mm pilot hole was drilled into the femur 502. The guide member 424 was then inserted into the pilot hole, and the blade 100 was advanced a distance of 20 mm into the femur 502. The blade reached the depth of 20 mm after about 7 seconds, and with minimal tooth damage.

Figure 31:
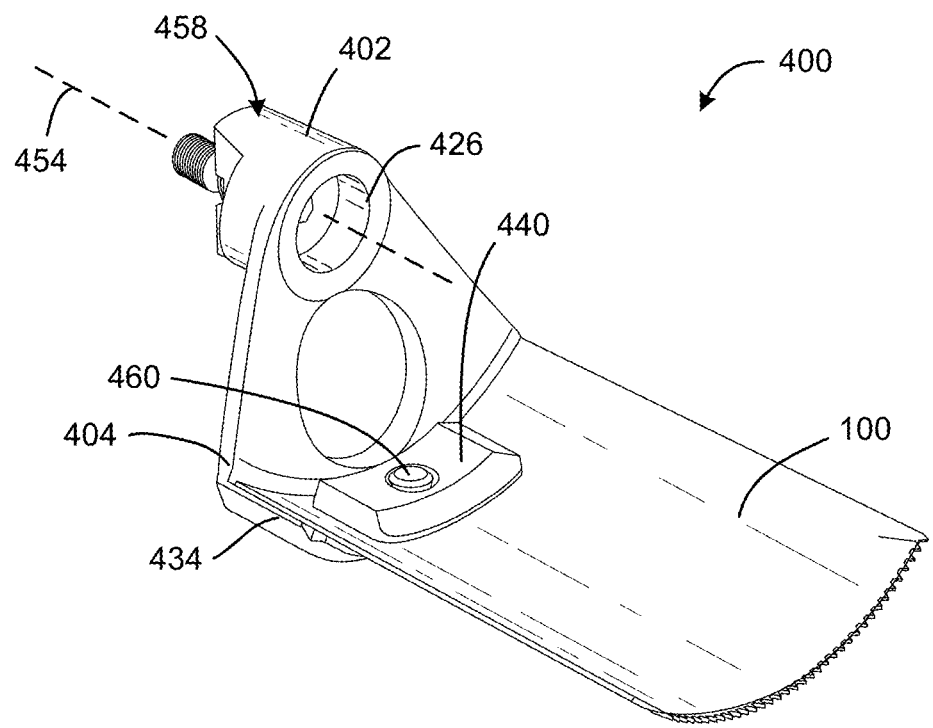
FIG. 31 is a perspective view of a hub assembly, according to another embodiment.
Figure 32:
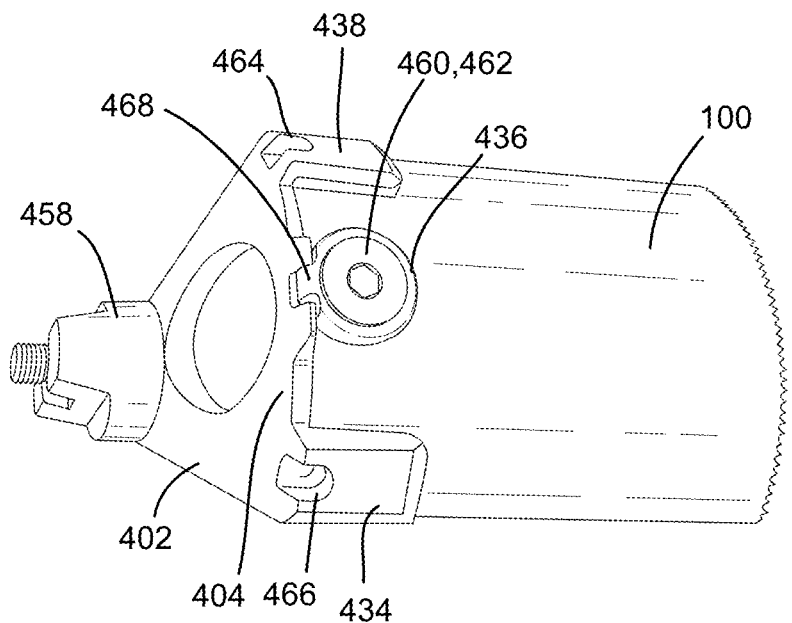
FIG. 32 is a perspective view of the hub assembly of FIG. 31 illustrating lower surfaces of the hub member and the blade.
Figure 33:
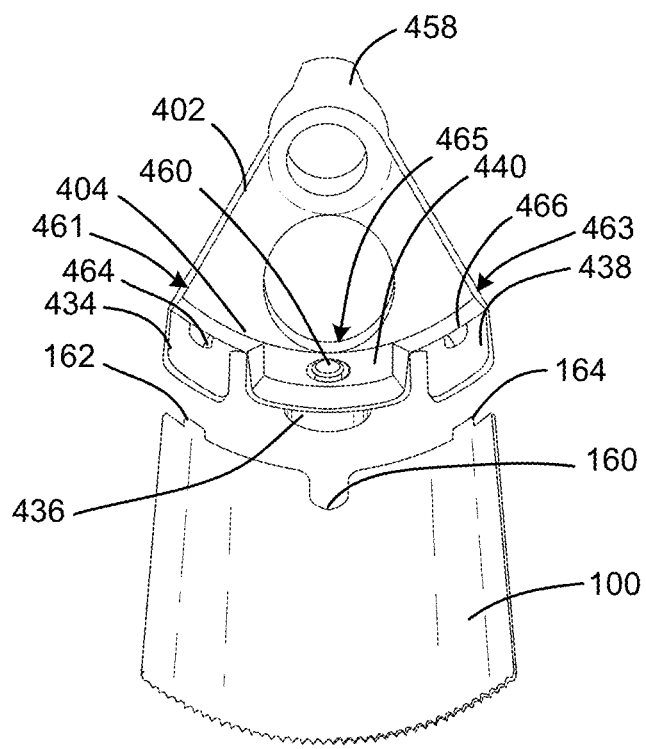
FIG. 33 is a perspective view of the hub assembly of FIG. 31 illustrating the blade separated from the hub member.
Figure 34:
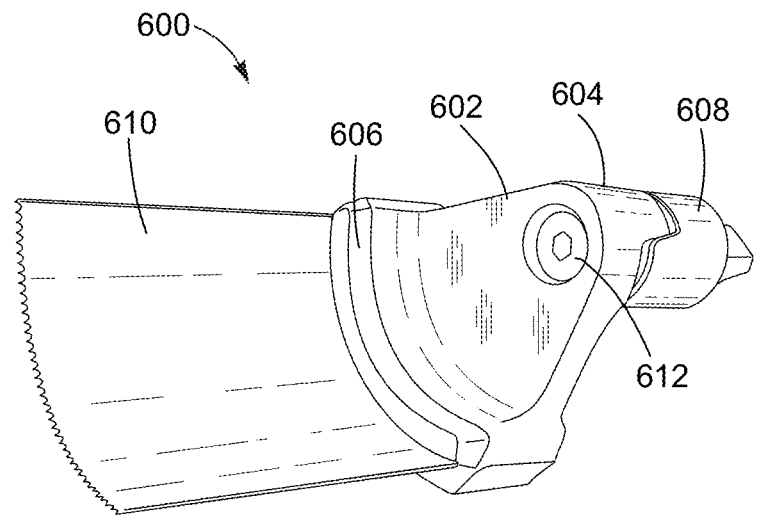
FIGS. 34 and 35 are perspective views of another embodiment of a hub assembly including a molded or additively manufactured hub member.
Figure 35:
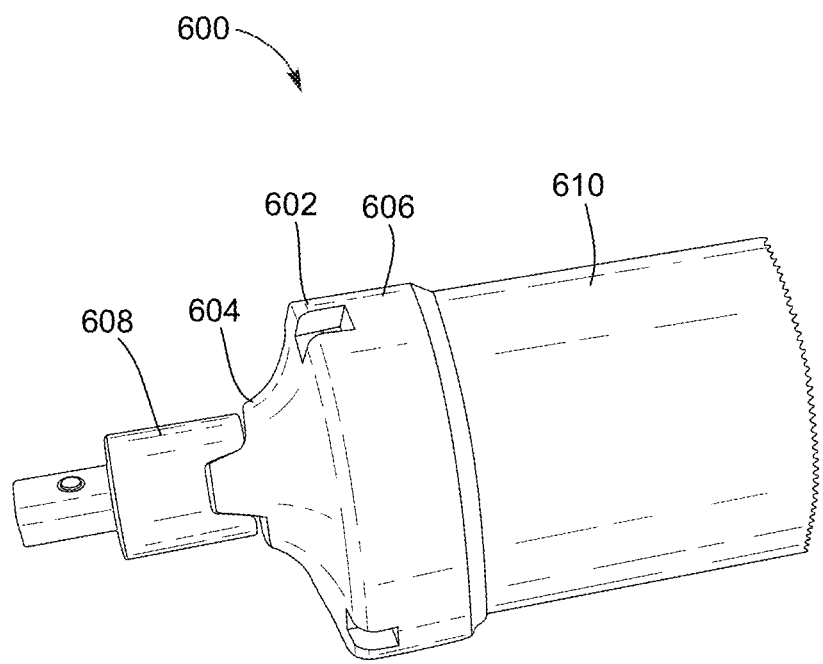
Figure 36:
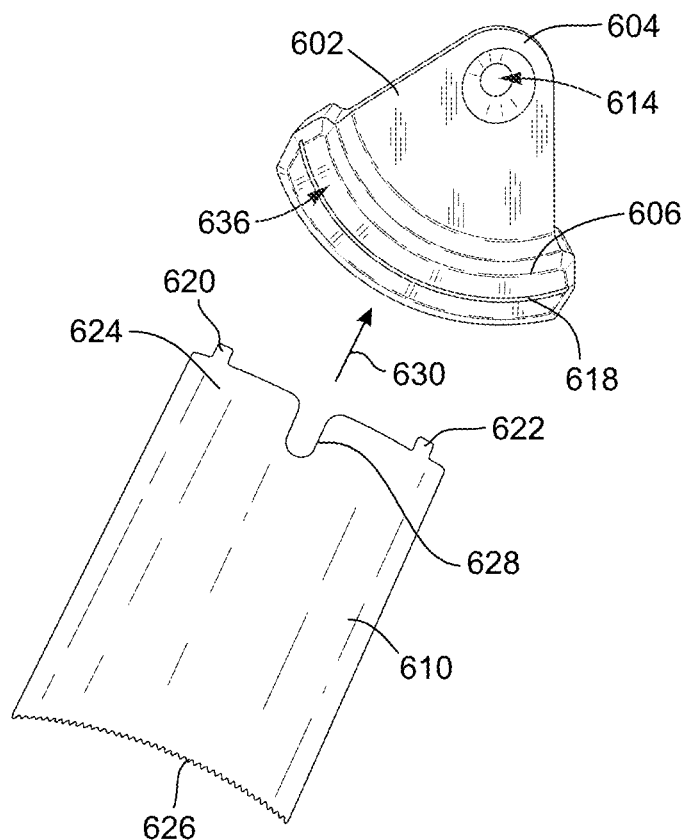
FIG. 36 is a perspective view illustrating attachment of the blade to the hub member of the hub assembly of FIG. 34.
Figure 37:
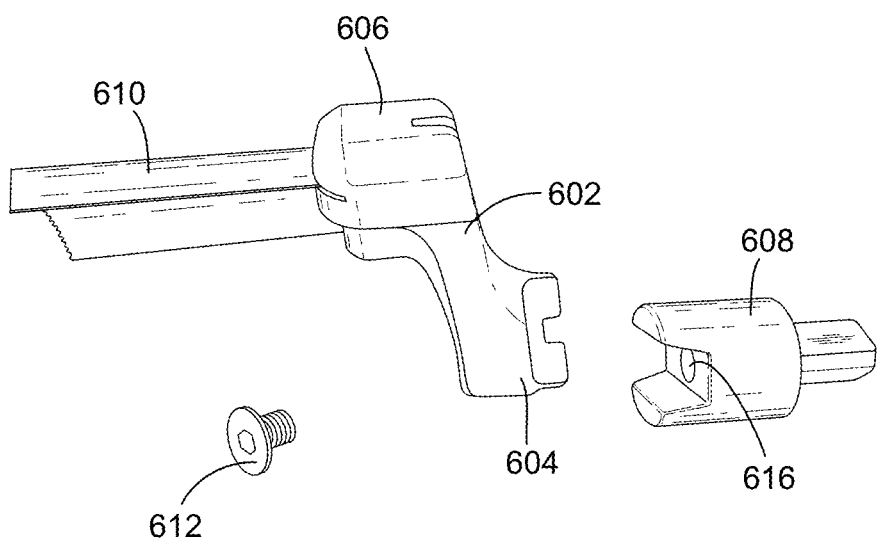
FIG. 37 is a perspective view illustrating the hub assembly of FIG. 34 prior to attachment of the chuck member.

FIGS. 31-33 illustrate another configuration of the hub assembly 400 similar to the embodiment of FIGS. 25A-29. Referring to FIGS. 31-33, the extension portions 434, 436, and 438 extend from the curved lower coupling portion 404 of the hub member 402. More particularly, with reference to FIG. 33, the extension portions 434 and 438 extend from respective lateral or side portions 461, 463 of the coupling portion 404, and the extension portions 436 and 440 can extend from a central portion 465 of the coupling portion. In the illustrated embodiment, the extension portion 440 extends from the coupling portion 404 above extension portion 436 such that the extension portions 436 and 440 are radially spaced apart from each other relative to the axis 454.

The extension portions 436 and 440 can be configured to receive a fastener configured as a set screw 460. As shown in FIG. 32, the lower extension portion 436 can have a round shape, and can receive the head 462 of the set screw 460 within a recess defined in the extension portion 436. In certain embodiments, the lower extension portion 436 can include an anti-rotation feature configured as an anti-rotation tab 468. The anti-rotation tab 468 can be configured to prevent detachment of the blade 100 from the hub assembly due to vibration. With reference to FIG. 33, the blade 100 can include a corresponding U-shaped notch or recess 160 at or near the center of the proximal edge portion of the blade and extending distally from the proximal edge portion.

As shown in FIG. 33, the extension portions 434, 438 can each define a respective opening or slot 464, 466, and the blade 100 can include corresponding extension portions or tabs 162, 164 spaced apart from each other along the proximal edge of the blade. To secure the blade 100 to the hub 402, the proximal end portion of the blade 100 can be inserted between the lower extension portion 436 and the upper extension portion 440 such that the shank of the set screw 460 is received in the recess 160 of the blade, and such that the tabs 162, 164 are received in the corresponding openings 464, 466, as shown in FIGS. 31 and 32. The set screw 460 can then be tightened to secure or clamp the blade between the extension portion 436 and the extension portion 440.

FIGS. 34-39A illustrate another embodiment of a hub assembly 600 including a hub member 602 and a blade member 610 coupled to the hub member 602. The hub member 602 can include an upper portion configured as a hub portion 604 and a lower portion configured as a coupling portion 606. The hub portion 604 can be coupled to a chuck member 608 similar to the chuck 410 of FIG. 21. As best illustrated in FIGS. 34-37, the chuck member 608 can be coupled to the hub portion 604 with a threaded fastener 612 that extends through an opening 614 (FIG. 36) in the hub portion and engages corresponding threads in an opening 616 (FIG. 37) defined in the chuck member 608. The coupling portion 606 can extend outwardly from the hub member 602, and can be configured to receive the blade 610, which can be configured according to any of the blade embodiments described herein.

Figure 39:
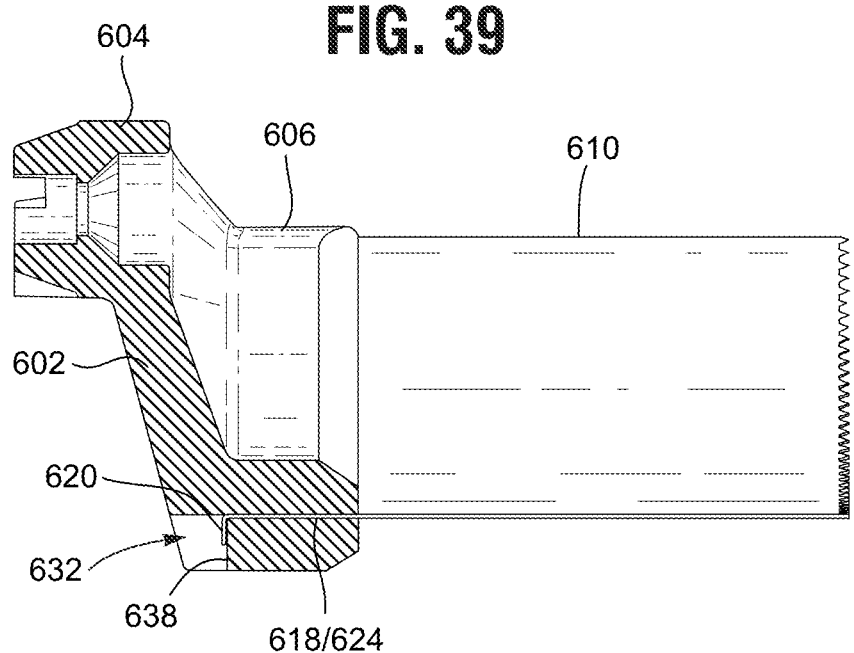
FIGS. 39 and 39A are a cross-sectional side views of the hub assembly of FIG. 34.
Figure 39A:
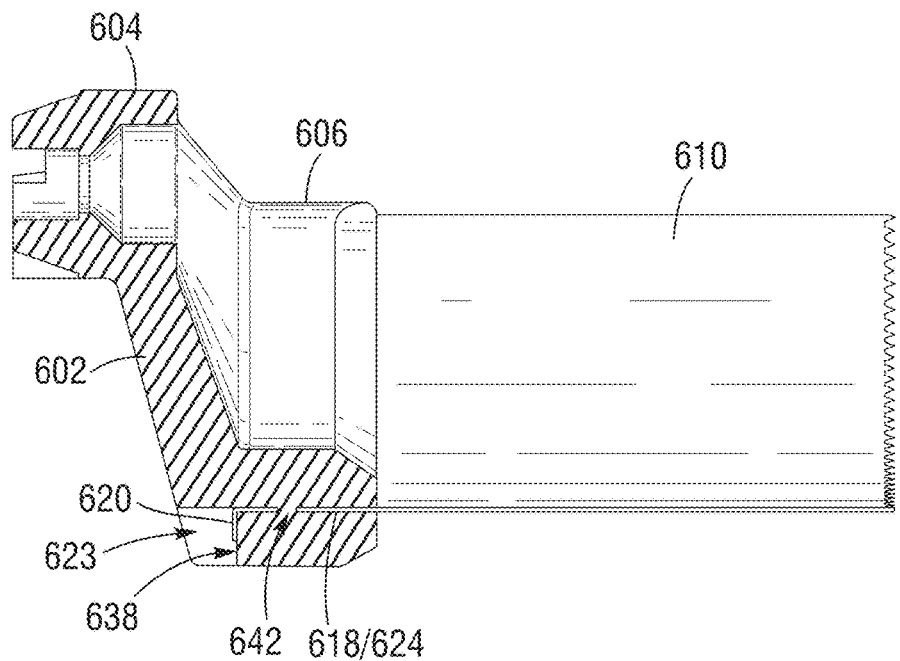

In certain configurations, the hub member 602 can be made by injection molding, or by an additive manufacturing process. For example, in some embodiments the hub member 602 can be three-dimensionally printed ("3D printed") from any of a variety of polymeric or metallic materials. The blade 610 can be coupled to the coupling portion 606 during the printing process, or after the printing of the hub member 602 is complete. For example, with reference to FIG. 36, in certain embodiments the coupling portion 606 can define a channel or slot 618 in an outwardly facing or distal surface 636 of the coupling portion and extending along a length of the coupling portion 606. In the illustrated configuration, the slot 618 is curved to match the curvature of the coupling portion and/or the curvature of the blade 610. As shown in FIG. 39, the slot 618 can extend inwardly from the surface 636 through at least a portion of the thickness of the coupling portion 606.

Referring again to FIG. 36, the blade 610 can include a plurality of tab portions extending from a proximal edge portion 624 of the blade opposite the blade teeth 626, similar to the blade 100 of FIG. 33. In the illustrated embodiment, the blade includes two tab portions 620, 622, although the blade may include more or fewer tabs, depending upon the particular application. The blade 610 can also include a recess or slot 628 defined on the proximal edge 624 (allowing the blade to be used, for example, with the hub member of FIG. 33). In certain embodiments, once the hub member 602 has been printed or otherwise formed, the proximal edge 624 of the blade 610 can be inserted into the slot 618 in the manner indicated by arrow 630. In certain configurations, the blade can be press-fitted into the slot 618.

Figure 38:
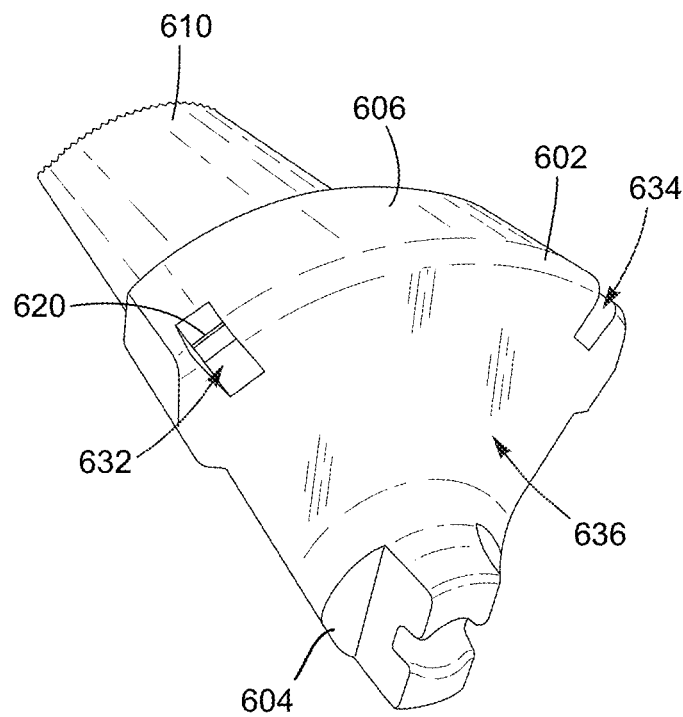
FIG. 38 is a rear perspective view of the hub assembly of FIG. 34 illustrating a proximal surface of the hub member.

With reference to FIG. 38, the rear or proximal surface 640 of the hub member 602 can include recesses or openings 632, 634 corresponding to the tab portions 620, 622 of the blade 610. As best shown in FIG. 39, the openings 632, 634 can extend distally through the body of the hub member such that the openings 632, 634 are in fluid communication with the slot 618. Thus, when the blade 610 is inserted into the slot 618, the tabs 620 and 622 can extend into the respective openings 632 and 634. The tab portions 620 and 622 can then be bent or folded over to engage the hub member. For example, in the illustrated configuration, the tab portions 620, 622 can engage respective interior surfaces, walls, or shoulders 638 of the openings to hold the blade 610 in place. In the illustrated configuration, the shoulders 638 are recessed within the openings 632, 634. However, in other embodiments, the hub assembly can be configured such that the tab portions 620, 622 engage the proximal surface 640 of the hub member 602.

In some embodiments, once the tab portions 620 and 622 have been folded to engage the shoulders 638, the hub member-blade assembly can then be pressed or rolled to further compress or form the material of the coupling portion 606 around the blade 610 to hold the blade in place. The hub member 602 can also include more or fewer openings corresponding to the number of tab portions of the blade, as desired. In other configurations, the hub member and blade can be configured such that the entire proximal edge portion 624 of the blade is folded over a shoulder or surface of the hub member.

In another embodiment, the blade 610 can be coupled or inserted into or on the coupling portion 606 of the hub member 602 during the printing process. For example, a portion of the coupling portion 606 of the hub member 602 can be printed, and the blade 610 can be situated on the partially printed coupling portion. The remainder of the hub member 602 can then be printed around the blade 610 to capture the blade and create a one-piece, unitary construction. The tab portions 620 and 622 of the blade 610 can also be inserted into the openings 632 and 634 of the hub member and folded to engage the hub member, as described above, before the printing of the hub member resumes. In certain embodiments, the blade 610 can also include one or more openings (e.g., similar to the openings 152, 154 of FIG. 25B) on the proximal end portion 624 of the blade through which the material of the hub member 602 can flow or extend when printed or injection molded, as indicated schematically at 642 in FIG. 39A. This can allow the hub member 602 to mechanically interlock with the blade 610.

In certain embodiments, the chuck member 608 can be integrally formed with the hub member 602, or can be separately attachable to the hub member. As used herein, the terms "integrally formed" and "unitary construction" refer to a construction that does not include any welds, fasteners, or other means for securing separately formed pieces of material to each other. For example, in some embodiments, the chuck member 608 can be 3D printed with the hub member 602. In other embodiments, the chuck member 608 can be made separately (e.g., from a metal, ceramic, or polymeric material), and attached to the hub member 602. In certain embodiments, the hub member 602 may also include an internal scaffolding structure around which the hub member is printed. In certain embodiments, the hub assembly 600 can be configured for use with a guide member similar to the guide member 424 of FIG. 21.

In addition to the configurations and cutting structures described above, the blades described herein, such as the blade 100 and the blade 610, can also provide a number of significant advantages related to blade material and thickness. For example, conventional stainless steel radial saw blades are typically heat-treated to harden the metal. For example, a conventional blade may be made from 17-4 PH stainless steel heat-treated to have a Rockwell hardness of 38 HRC to 44 HRC. The steel of such blades often exhibits elongation of 7% or less, and has high brittleness properties. This can make the blades prone to breaking under bending loads, and requires that the blades have a thickness of greater than 0.02 inch, such as 0.03 inch or more, in order to compensate for the high brittleness of the metal.

In contrast, the blade embodiments described herein can be made from cold-drawn stainless steel sheet stock, such as type 316 cold-drawn stainless steel, without heat treatment. Blades made from such cold-drawn steel exhibit high ductility properties, such as elongation of 15% or more, which is more than double the elongation exhibited by traditional steel blades. Moreover, the blades can also have a Rockwell hardness of from 38 HRC to 45 HRC. Thus, the blades described herein can exhibit both high ductility and high hardness properties. The high ductility allows the blades to be made significantly thinner than existing blades with a surprising ability to endure bending loads without fracture, as further described below. The high hardness provides cutting efficiency and resistance to wear typically associated only with heat-treated blades of greater thickness.

As stated above, the combination of the high ductility and high hardness parameters above allow the blades described herein to be made surprisingly thin. For example, in some embodiments, the blades can have a thickness of 0.02 inch or less. In some embodiments, the blades can have a thickness of from about 0.005 inch to about 0.018 inch. In particular embodiments, the blades can have a thickness of about 0.012 inch. The reduced thickness of the blade allows the radius of the cut bone surface to precisely match the radius of the surface of the excised bone segment, as described above, while the high ductility properties of the metal improve the blade's fracture resistance. Blades with thicknesses in this range can also offer advantages such as a reduced tendency to "walk" or "jump" across the bone surface when initiating a cut, as compared to blades with higher thicknesses. In certain embodiments, the thickness of the blades can vary along the width of the blade, as in certain configurations described above, or can be constant along the blade width, depending upon the particular characteristics desired.

Figure 40A:
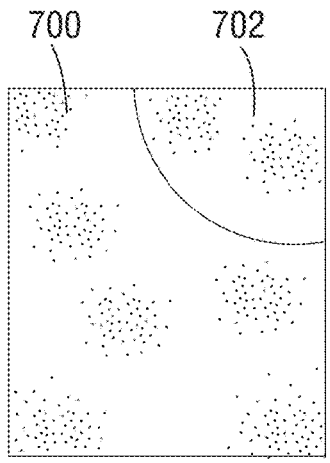
FIG. 40A is a side elevation view illustrating a cut made in a foam block using an embodiment of a radial saw blade having a thickness of 0.012 inch.

FIG. 40A illustrates a cut made in a foam block 700 with a blade according to the embodiments described herein having a thickness of about 0.012 inch (0.3 mm). As illustrated in FIG. 40A, the relatively small thickness of the blade results in a small gap between the main foam block 700 and a segment 702 cut from the block. The radii of the cut surfaces on the block 700 and on the segment 702 are closely matched along the full length of the cut. In the context of a bone, this reduces the tendency of the segment to move with respect to the bone, thereby reducing the risk that the bone and the segment fail to unite post-operatively.

Figure 40B:
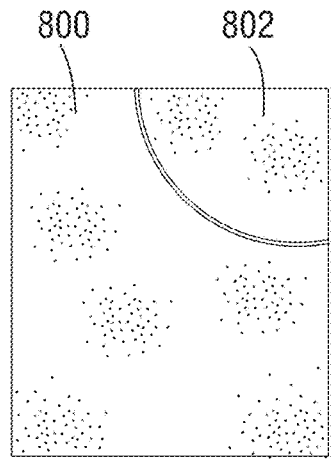
FIGS. 40B and 40C are side elevation views illustrating cuts made in foam blocks using conventional saw blades.
Figure 40C:
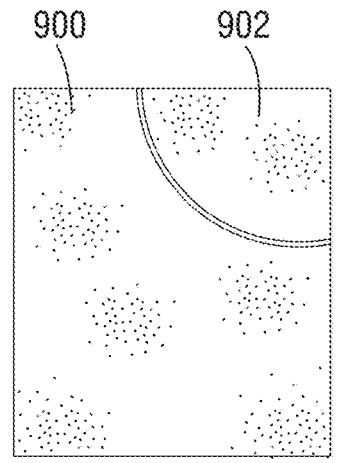

FIG. 40B illustrates a similar cut made in a block 800 using a blade having a thickness of 0.0197 inch (0.5 mm), and FIG. 40C illustrates a cut made in a block 900 using a blade having a thickness of 0.031 inch (0.8 mm). Relatively large gaps can be seen between the respective blocks 800, 900, and the segments 802, 902 cut from them, and the radii of the cut surfaces do not match as closely as in the cut illustrated in FIG. 40A. Such gaps and mismatches in surface radii can significantly increase the risk of non-union outcomes in osteotomy procedures, and can be addressed by the blade embodiments described herein having thicknesses of 0.02 inch or less.

Figure 41:
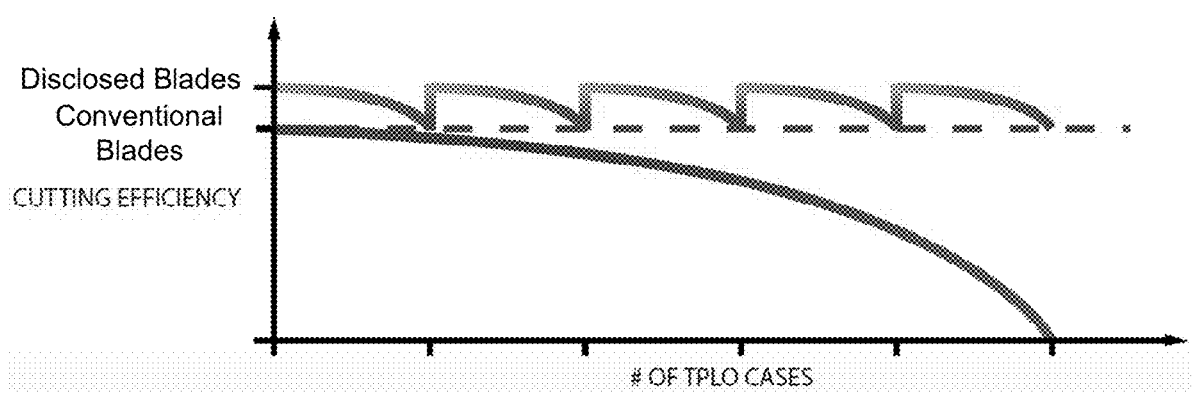
FIG. 41 is a graph illustrating the decline in cutting efficiency of a saw blade as the number of uses increases.

The blades described herein can also be cost-effectively manufactured. For example, the blades described herein can be made by acid etching or stamping metal sheet stock. This can significantly lower the cost and complexity of manufacturing compared to existing blades, which are typically machined from bar stock. Because the blade and hub embodiments described herein can be cost-effectively manufactured, they can also be cost-effectively replaced before the cutting efficiency of the blades degrades below a desired threshold. For example, FIG. 41 illustrates the decline in cutting efficiency of a conventional blade as a function of the number of TPLO osteotomies performed. The replaceable blade designs described herein allow the blades to be replaced quickly and cost-effectively before the cutting efficiency of the blades declines below a surgeon's preferred threshold, which can avoid complications such as binding, overheating of the bone, etc.

Additionally, although the blade and hub embodiments of the present application are described with reference to veterinary medical applications, it should be understood that the blades, hubs, and manufacturing techniques are also applicable to instruments in other disciplines, such as human medical instruments.

General Considerations

As used herein, the term "proximal" refers to a direction toward the point of origin or attachment, frequently toward the user in the context of a surgical instrument.

As used herein, the term "distal" refers to a direction away from the point of origin or attachment, frequently away from the user in the context of a surgical instrument.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

The invention claimed is:

1. A saw blade, comprising:
a curved main body including a first surface, a second surface on an opposite side of the curved main body from the first surface, a proximal edge portion, a distal edge portion, and first and second side portions extending between the proximal and distal edge portions;
wherein the proximal edge portion is configured for coupling to a rotatable hub such that the saw blade is held in a curved shape with the first surface defining an outer radius when the saw blade is coupled to the rotatable hub;
wherein the distal edge portion comprises a plurality of cutting teeth; and
wherein the saw blade comprises cold-drawn stainless steel without heat treatment, and has a thickness of 0.005 inch to 0.018 inch.

2. The saw blade of claim 1, wherein the saw blade comprises a Rockwell hardness of 38 HRC to 45 HRC and an elongation of at least 15%.

3. The saw blade of claim 1, wherein the saw blade is a radial saw blade configured for performing a tibial plateau leveling osteotomy (TPLO).

4. The saw blade of claim 1, wherein the proximal edge portion further comprises first and second tab portions extending proximally from the proximal edge portion and spaced apart from each other along the proximal edge portion.

5. The saw blade of claim 4, wherein the first tab portion is offset from the first side portion of the saw blade toward a longitudinal axis of the curved main body, and the second tab portion is offset from the second side portion toward the longitudinal axis of the curved main body.

6. The saw blade of claim 1, wherein the proximal edge portion comprises a recess extending distally from the proximal edge portion.

7. The saw blade of claim 6, wherein the proximal edge portion comprises first and second tab portions extending proximally from the proximal edge portion, and the first and second tab portions are offset from the recess along the proximal edge portion of the saw blade.

8. The saw blade of claim 6, wherein the curved main body comprises first and second openings defined on opposite sides of the recess.

9. The saw blade of claim 1, wherein the second surface comprises a cutting structure configured such that a radius of an arc swept by the cutting structure when the saw blade is rotated is substantially equal to the outer radius of the first surface.

10. A method, comprising making the saw blade of claim 1 by acid etching.

11. The saw blade of claim 1, wherein the saw blade comprises type 316 cold-drawn stainless steel.

12. A surgical cutting assembly, comprising:
a hub member including a hub portion and a curved coupling portion, the coupling portion being radially offset from the hub portion with respect to a longitudinal axis of the hub portion about which the hub member is configured to rotate; and
a saw blade coupled to the coupling portion of the hub member, the saw blade comprising a curved main body including a first surface, a second surface on an opposite side of the curved main body from the first surface, a proximal edge portion, a distal edge portion comprising a plurality of cutting teeth, and first and second side portions extending between the proximal and distal edge portions, the proximal edge portion being coupled to the hub member such that the saw blade is held in a curved shape with the first surface defining an outer radius when the saw blade is coupled to the hub member, wherein the saw blade comprises cold-drawn stainless steel without heat treatment, and has a thickness of 0.005 inch to 0.018 inch.

13. The surgical cutting assembly of claim 12, wherein the coupling portion of the hub member comprises a plurality of extension portions that extend in the direction of the longitudinal axis of the hub member and contact and support the saw blade.

14. The surgical cutting assembly of claim 13, wherein the coupling portion of the hub member comprises three extension portions including a first side extension portion, a second side extension portion, and a third central extension portion between the first and second side extension portions.

15. The surgical cutting assembly of claim 14, wherein the third central extension portion is configured to receive a fastener.

16. The surgical cutting assembly of claim 14, wherein the third central extension portion is offset from the first side extension portion and the second side extension portion such that the first and second side extension portions of the hub member contact the first surface of the saw blade and the third central extension portion contacts the second surface of the saw blade.

17. The surgical cutting assembly of claim 14, wherein the first side extension portion of the hub member defines an opening configured to receive a tab portion of the saw blade.

18. The surgical cutting assembly of claim 12, wherein the hub member comprises an injection molded or additively manufactured polymeric material.

19. The surgical cutting assembly of claim 18, wherein the saw blade includes at least one tab portion extending through the coupling portion of the hub member and folded over to engage the hub member.

20. The surgical cutting assembly of claim 12, wherein the saw blade includes at least one tab portion extending through an opening defined in the coupling portion of the hub member.

21. A surgical cutting assembly, comprising:
a hub member including a hub portion and a curved coupling portion, the coupling portion being radially offset from the hub portion with respect to a longitudinal axis of the hub portion about which the hub member is configured to rotate, the coupling portion including a first extension portion extending from a first side portion of the coupling portion, a second extension portion extending from a second side portion of the coupling portion opposite the first side portion, a third extension portion extending from a central portion of the coupling portion, and a fourth extension portion extending from the central portion and offset from the third extension portion such that the third and fourth extension portions are spaced apart from each other relative to the longitudinal axis of the hub portion;

a blade comprising a curved main body including a first surface, a second surface on an opposite side of the curved main body from the first surface, a proximal edge portion, a distal edge portion, and first and second side portions extending between the proximal and distal edge portions, the blade being coupled to the hub member such that the blade is situated on the first and second extension portions and held in a curved shape, and the proximal edge portion is received between the third and fourth extension portions of the hub member, the distal edge portion of the blade comprising a plurality of cutting teeth, the blade comprising cold-drawn stainless steel without heat treatment and having a thickness of 0.005 inch to 0.018 inch; and a fastener extending through the third extension portion, the blade, and the fourth extension portion to secure the blade to the hub member.

* * * * *